(12) United States Patent
Alvarado et al.

(10) Patent No.: US 10,694,994 B2
(45) Date of Patent: Jun. 30, 2020

(54) TECHNIQUES FOR JOINTLY CALIBRATING LOAD AND AEROBIC CAPACITY

(71) Applicant: Apple Inc., Cupertino, CA (US)

(72) Inventors: Alexander Singh Alvarado, Mountain View, CA (US); Craig H. Mermel, San Jose, CA (US); Hung A. Pham, Oakland, CA (US); Karthik Jayaraman Raghuram, Cupertino, CA (US); Xing Tan, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 502 days.

(21) Appl. No.: 15/466,397

(22) Filed: Mar. 22, 2017

(65) Prior Publication Data

US 2017/0273619 A1    Sep. 28, 2017

Related U.S. Application Data

(60) Provisional application No. 62/311,479, filed on Mar. 22, 2016.

(51) Int. Cl.
*A61B 5/00* (2006.01)
*A61B 5/0205* (2006.01)
(Continued)

(52) U.S. Cl.
CPC .......... *A61B 5/4884* (2013.01); *A61B 5/0205* (2013.01); *A61B 5/02444* (2013.01);
(Continued)

(58) Field of Classification Search
None
See application file for complete search history.

(56) References Cited

U.S. PATENT DOCUMENTS 4,566,461 A    1/1986   Marks
5,158,093 A    10/1992  Reibold
(Continued)

FOREIGN PATENT DOCUMENTS

GB    2465824 A       6/2010
JP    2010-051333 A   3/2010
(Continued)

OTHER PUBLICATIONS

Le, et al., "Sensor-based Training Optimization of a Cyclist Group", Seventh International Conference on Hybrid Intelligent Systems, IEEE 2007, pp. 265-270.
(Continued)

*Primary Examiner* — Michael R Bloch
(74) *Attorney, Agent, or Firm* — DLA Piper LLP

(57) ABSTRACT

A relationship relating a load of exercise and a user's aerobic capacity may be determined as follows. A processor circuit of a device may retrieve, from a memory, a prior probability distribution of the load of exercise and a prior probability distribution of the user's aerobic capacity. The processor circuit may compute a joint prior probability of the load of exercise and the user's aerobic capacity. The processor circuit may compute a joint likelihood of the load of exercise and the user's aerobic capacity based on data indicative of a measured time-stamped work rate and a measured time-stamped heart rate. The processor circuit may combine the joint prior probability and the joint likelihood to produce a joint posterior probability. The processor circuit may use the joint posterior probability to determine a relationship relating the load of exercise and the user's aerobic capacity and output a calorie calculation.

24 Claims, 10 Drawing Sheets

(51) Int. Cl.
  *A61B 5/024* (2006.01)
  *A61B 5/083* (2006.01)
  *A61B 5/11* (2006.01)
(52) U.S. Cl.
  CPC ............ *A61B 5/083* (2013.01); *A61B 5/1118* (2013.01); *A61B 5/681* (2013.01); *A61B 2562/085* (2013.01)

(56) References Cited

U.S. PATENT DOCUMENTS

| | | |
|---|---|---|
| 5,663,897 A | 9/1997 | Geiser |
| 6,013,008 A | 1/2000 | Fukushima |
| 6,059,724 A | 5/2000 | Campell et al. |
| 6,582,380 B2 | 6/2003 | Woolery et al. |
| 6,687,535 B2 | 2/2004 | Hautala et al. |
| 6,837,827 B1 | 1/2005 | Lee et al. |
| 6,868,338 B1 | 3/2005 | Elliott |
| 7,254,516 B2 | 8/2007 | Case, Jr. et al. |
| 7,311,675 B2 | 12/2007 | Peifer et al. |
| 7,467,060 B2 | 12/2008 | Kulach et al. |
| 7,534,206 B1 | 5/2009 | Lovitt et al. |
| 7,690,556 B1 | 4/2010 | Kahn et al. |
| 7,771,320 B2 | 8/2010 | Riley et al. |
| 7,805,149 B2 | 9/2010 | Werner et al. |
| 7,841,967 B1 | 11/2010 | Kahn et al. |
| 8,290,480 B2 | 10/2012 | Abramson et al. |
| 8,483,775 B2 | 7/2013 | Buck et al. |
| 8,589,174 B2 | 11/2013 | Nelson et al. |
| 8,892,391 B2 | 11/2014 | Tu et al. |
| 8,894,576 B2 | 11/2014 | Alwan et al. |
| 8,911,329 B2 | 12/2014 | Lin et al. |
| 9,413,871 B2 | 8/2016 | Nixon et al. |
| 9,526,430 B2 | 12/2016 | Srinivas et al. |
| 9,788,794 B2 | 10/2017 | Le Boeuf et al. |
| 10,188,347 B2 | 1/2019 | Self et al. |
| 10,206,627 B2 | 2/2019 | Le Boeuf et al. |
| 10,219,708 B2 | 3/2019 | Altini |
| 10,292,606 B2 | 5/2019 | Wisbey et al. |
| 2001/0022828 A1 | 9/2001 | Pyles |
| 2002/0019585 A1 | 2/2002 | Dickinson |
| 2003/0032460 A1 | 2/2003 | Cannon et al. |
| 2003/0138763 A1 | 7/2003 | Roncalez et al. |
| 2004/0064061 A1 | 4/2004 | Nissila |
| 2005/0107723 A1 | 5/2005 | Wehman et al. |
| 2006/0064277 A1 | 3/2006 | Jung et al. |
| 2006/0136173 A1 | 6/2006 | Case et al. |
| 2006/0190217 A1* | 8/2006 | Lee ......................... G05B 13/04 702/181 |
| 2006/0217231 A1 | 9/2006 | Parks et al. |
| 2007/0100666 A1 | 5/2007 | Stivoric et al. |
| 2007/0150229 A1 | 6/2007 | Fujiwara |
| 2007/0219059 A1* | 9/2007 | Schwartz ............. A61B 5/0205 482/8 |
| 2007/0275825 A1 | 11/2007 | O'Brien |
| 2007/0276271 A1* | 11/2007 | Chan ................. A61B 5/02438 600/509 |
| 2008/0096726 A1 | 4/2008 | Riley et al. |
| 2008/0214360 A1 | 9/2008 | Stirling et al. |
| 2009/0009320 A1 | 1/2009 | O'Connor et al. |
| 2009/0024332 A1* | 1/2009 | Karlov ................. G06Q 50/22 702/19 |
| 2009/0043531 A1 | 2/2009 | Kahn et al. |
| 2009/0063099 A1 | 3/2009 | Counts et al. |
| 2010/0030350 A1 | 2/2010 | House et al. |
| 2010/0130890 A1 | 5/2010 | Matsumura et al. |
| 2010/0184564 A1 | 7/2010 | Molyneux et al. |
| 2010/0204952 A1 | 8/2010 | Irlam et al. |
| 2010/0210953 A1 | 8/2010 | Sholder et al. |
| 2010/0210975 A1 | 8/2010 | Anthony, III et al. |
| 2010/0217099 A1 | 8/2010 | Leboeuf et al. |
| 2010/0274102 A1* | 10/2010 | Teixeira ............. A61B 5/14552 600/301 |
| 2010/0298656 A1 | 11/2010 | McCombie et al. |
| 2011/0040193 A1 | 2/2011 | Seppanen et al. |
| 2011/0054359 A1 | 3/2011 | Sazonov et al. |
| 2011/0082008 A1 | 4/2011 | Cheung et al. |
| 2011/0131012 A1 | 6/2011 | Czaja et al. |
| 2011/0152695 A1 | 6/2011 | Granqvist et al. |
| 2011/0195707 A1 | 8/2011 | Faerber et al. |
| 2011/0238485 A1 | 9/2011 | Haumont et al. |
| 2011/0301436 A1* | 12/2011 | Teixeira ............... A61B 5/0402 600/301 |
| 2012/0083715 A1 | 4/2012 | Friedman |
| 2012/0172677 A1 | 7/2012 | Beith |
| 2012/0238832 A1 | 9/2012 | Hwang |
| 2012/0296455 A1 | 11/2012 | Ohnemus et al. |
| 2012/0322621 A1 | 12/2012 | Bingham et al. |
| 2013/0023739 A1 | 1/2013 | Russell |
| 2013/0041590 A1 | 2/2013 | Burich et al. |
| 2013/0053990 A1* | 2/2013 | Ackland ............... G06Q 30/02 700/91 |
| 2013/0096943 A1 | 4/2013 | Carey et al. |
| 2013/0158686 A1 | 6/2013 | Zhang et al. |
| 2013/0178335 A1 | 7/2013 | Lin et al. |
| 2013/0197377 A1 | 8/2013 | Kishi et al. |
| 2013/0218053 A1 | 8/2013 | Kaiser et al. |
| 2013/0267794 A1 | 10/2013 | Fernstrom et al. |
| 2014/0073486 A1* | 3/2014 | Ahmed ............... A61B 5/02405 482/9 |
| 2014/0087708 A1 | 3/2014 | Kalita et al. |
| 2014/0088444 A1 | 3/2014 | Saalasti et al. |
| 2014/0107932 A1 | 4/2014 | Luna |
| 2014/0109390 A1 | 4/2014 | Manning |
| 2014/0121471 A1 | 5/2014 | Walker |
| 2014/0167973 A1 | 6/2014 | Letchner et al. |
| 2014/0172238 A1 | 6/2014 | Craine |
| 2014/0197946 A1 | 7/2014 | Park et al. |
| 2014/0200906 A1 | 7/2014 | Bentley et al. |
| 2014/0207264 A1 | 7/2014 | Quy |
| 2014/0213920 A1* | 7/2014 | Lee ..................... A61B 5/222 600/509 |
| 2014/0221854 A1 | 8/2014 | Wai |
| 2014/0228649 A1 | 8/2014 | Rayner et al. |
| 2014/0244071 A1 | 8/2014 | Czaja et al. |
| 2014/0266789 A1 | 9/2014 | Matus |
| 2014/0276127 A1 | 9/2014 | Ferdosi et al. |
| 2014/0278139 A1 | 9/2014 | Hong et al. |
| 2014/0278229 A1 | 9/2014 | Hong et al. |
| 2014/0316305 A1 | 10/2014 | Venkatraman et al. |
| 2014/0348367 A1 | 11/2014 | Vavrus et al. |
| 2015/0087929 A1 | 3/2015 | Rapoport et al. |
| 2015/0088006 A1 | 3/2015 | Rapoport et al. |
| 2015/0100141 A1 | 4/2015 | Hughes |
| 2015/0119728 A1 | 4/2015 | Blackadar et al. |
| 2015/0148632 A1* | 5/2015 | Benaron ............... A61B 5/0059 600/322 |
| 2015/0250417 A1 | 9/2015 | Cheng et al. |
| 2015/0256689 A1 | 9/2015 | Erkkila et al. |
| 2015/0260514 A1 | 9/2015 | Menelas et al. |
| 2015/0327804 A1 | 11/2015 | Lefever et al. |
| 2015/0328523 A1 | 11/2015 | Heling et al. |
| 2015/0338926 A1 | 11/2015 | Park et al. |
| 2015/0345985 A1 | 12/2015 | Fung et al. |
| 2015/0357948 A1 | 12/2015 | Goldsten |
| 2015/0374240 A1 | 12/2015 | Lee |
| 2016/0021238 A1 | 1/2016 | Abramson et al. |
| 2016/0057372 A1 | 2/2016 | Iwane et al. |
| 2016/0058302 A1 | 3/2016 | Raghuram et al. |
| 2016/0058329 A1 | 3/2016 | Srinivas et al. |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh Alvarado et al. |
| 2016/0058372 A1 | 3/2016 | Raghuram et al. |
| 2016/0059079 A1 | 3/2016 | Watterson |
| 2016/0084869 A1 | 3/2016 | Yuen et al. |
| 2016/0166178 A1 | 6/2016 | Fuss et al. |
| 2016/0170998 A1 | 6/2016 | Frank et al. |
| 2016/0206248 A1 | 7/2016 | Sartor et al. |
| 2016/0256058 A1 | 9/2016 | Pham et al. |
| 2016/0269572 A1 | 9/2016 | Erkkila et al. |
| 2016/0287177 A1 | 10/2016 | Huppert et al. |

(56) References Cited

U.S. PATENT DOCUMENTS

| | | |
|---|---|---|
| 2016/0361020 A1 | 12/2016 | LeBoeuf et al. |
| 2016/0363449 A1 | 12/2016 | Metzler et al. |
| 2016/0374614 A1 | 12/2016 | Cavallaro et al. |
| 2017/0007166 A1 | 1/2017 | Roover et al. |
| 2017/0061817 A1 | 3/2017 | Mettler May |
| 2017/0074897 A1 | 3/2017 | Mermel et al. |
| 2017/0082649 A1 | 3/2017 | Tu et al. |
| 2017/0094450 A1 | 3/2017 | Tu et al. |
| 2017/0111768 A1 | 4/2017 | Smith et al. |
| 2017/0188893 A1 | 7/2017 | Venkatraman et al. |
| 2017/0202486 A1 | 7/2017 | Martikka et al. |
| 2017/0251972 A1 | 9/2017 | Jayaraman et al. |
| 2017/0259116 A1 | 9/2017 | Mestas |
| 2017/0367658 A1 | 12/2017 | LeBoeuf et al. |
| 2018/0028863 A1 | 2/2018 | Matsuda |

FOREIGN PATENT DOCUMENTS

| | | |
|---|---|---|
| JP | 2013-039316 A | 2/2013 |
| JP | 2014-042757 A | 3/2014 |
| JP | 2016-150018 A | 8/2016 |
| JP | 2018-000543 A | 1/2018 |
| JP | 2018-015187 A | 2/2018 |
| WO | 2010/090867 A2 | 8/2010 |
| WO | 2011/105914 A1 | 9/2011 |
| WO | 2015/126182 A1 | 8/2015 |
| WO | 2015/200900 A1 | 12/2015 |
| WO | 2016/044831 A1 | 3/2016 |
| WO | 2016/073620 A1 | 5/2016 |

OTHER PUBLICATIONS

Your Fitness FAQ, Why is it important to warm up and cool down in a workout?, 2012, Web, Retrieved from: http://www.yourfitnessfaq.com/whyisitimportanttowarmupandcooldowninaworkout.html.

Wang et al., "Time constant of heart rate recovery after low level exercise as a useful measure of cardiovascular fitness," Conf. Proc. IEEE Eng. Meda Biol. Soc., vol. 1, pp. 1799-1802 : (2006).

Vella et al., "Exercise After-Burn: Research Update," 2005, Web, Retrieved from: http://www.unm.edu/~lkravitz/Article%20folder/epocarticle.html.

Tanaka et al., "Age-predicted maximal heart rate revisited," Journal of the American College of Cardiology, vol. 37, Issue 1, pp. 153-156 (Jan. 2001).

Song et al., "Training Activity Recognition Systems Online Using Real-Time Crowdsourcing," University of Rochester Computer Science, UbiCom' 12, Sep. 5-8, 2012 (2 pages).

Rowlands et al., "Assessing Sedentary Behavior with the GENEActiv: Introducing the Sedentary Sphere," Medicine and science in sports and exercise 46.6 (2014): 1235-1247.

Hasson et al., "Accuracy of four resting metabolic rate production equations: Effects of sex, body mass index, age, and race/ethnicity", Journal of Science and Medicine in Sport, 2011, vol. 14, p. 344-351.

Rapoport et al., "Metabolic Factors Limiting Performance in Marathon Runners," PLoS Computational Biology, vol. 6, Issue 10, 13 pages (Oct. 2010).

Noakes et al., "Lore of Running," Fourth Edition, Human Kinetics, Chapter 2: Oxygen Transport, Chapter 3: Energy Systems, 157 pages (2002).

Myers et al., "Exercise Capacity and Mortality Among Men Referred for Exercise Testing," The New Enqland Journal of Medicine, vol. 346, No. 11, pp. 793-801 (Mar. 14, 2002).

Mcardle et al., "Exercise Physiology: Nutrition, Energy and Human Performance," Seventh Edition, Lippincott Williams & Wilkins, Chapter 5: Introduction to Energy Transfer, Chapter 6: Energy Transfer in the Body, Chapter 7: Energy Transfer in Exercise, Chapter 8: Measurement of Human Energy Expenditure, Chapter 9: Human Energy Expenditure During Rest and Physical Activity, Chapter 10: Energy Expenditure During Walking, Jogging, running and Swimming, Chapter 11: Individual Differences and Measurement of Energy Capacities, Chapter 21: Training for Anaerobic and Aerobic Power.

Margaria et al., "Energy cost of running," Journal of Applied Physiology, vol. 18, No. 2, pp. 367-370 (Mar. 1, 1963).

Lucas et al., "Mechanisms of orthostatic intolerance following very prolonged exercise", 2008, J Appl Physiol, 105: 213-225.

Lavie et al., "Impact of cardiorespiratory fitness on the obesity paradox in patients with heartfailure," Mayo Clinic Proceedings, vol. 88, No. 3, pp. 251-258 (Mar. 2013).

Kunze et al., "Where am i: Recognizing on-body positions of wearable sensors," Location-and context-awareness. Springer Berlin Heidelberg, 2005. 264-275.

Keytel et al., "Prediction of energy expenditure from heart rate monitoring during submaximal exercise," 2005, Journal of Sports Sciences, 23(3):289-97.

Sabatini, "Kalman-filter-based orientation determination using inertial/magnetic sensors: observability analysis and performance evaluation," Sep. 27, 2011, Sensors 2011, 11, 9182-9206.

Jackson et al., "Prediction of functional aerobic capacity without exercise testing, Medicine and Science in Sports and Exercise," 22(6), 863-870, 1990.

Isaacs et al., Modeling energy expenditure and oxygen consumption in human exposure models: accounting for fatigue and EPOC, 2008, Journal of Exposure Science and Environmental Epidemiology, 18: 289-298.

Human Kinetics, Aerobic Workout Components, 2011, Web, Retrieved from: http://www.humankinetics.com/excerpts/excerpts/aerobicworkoutcomponentsexcerpt.

Glass et al., "ACSM's Metabolic Calculations Handbook," Lippincott Williams & Wilkins, 124 pages. (2007).

Gao et al., "Evaluation of accelerometer based multi-sensor versus single-sensor activity recognition systems," Medical engineering & physics 36.6 (2014): 779-785.

Fox et al., "Physical Activity and the Prevention of Coronary Heart Disease," Bull. N.Y. Acad. Med., vol. 44, No. 8, pp. 950-967 (Aug. 1968).

Earnest et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 paces (Mar. 2013).

Frankenfield et al., "Comparison of Predictive Equations for Resting Metabolic Rate in Healthy Nonobese and Obese adults: A systematic review," Journal of the American Dietetic Association, May 2005, vol. 105, No. 5, p. 775-789.

Chu, "In-Vehicle Driver Detection Using Mobile Phone Sensors, Submitted for Graduation with departmental Distinction in Electrical and Computer Engineering," Apr. 20, 2011, pp. 1-21.

Cavanagh et al., "The effect of stride length variation on oxygen uptake during distance running," Medicine and Science in Sports and Exercise, vol. 14, No. 1, pp. 30-35 (1982).

Burke et al., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).

Bruce, RA et al., "Exercising testing in adult normal subjects and cardiac patients," Pediatrics, vol. 32, No. Suppl., pp. 742-756 (Oct. 1963).

Bruce, R.A. et al., "Maximal oxygen intake and nomographic assessment of functional aerobic impairment in cardiovascular disease," American Heart Journal, vol. 85, Issue 4, pp. 546-562 (Apr. 1973).

Brooks, GA et al., "Exercise Physiology: Human Bioenergetics and Its Applications," Fourth Edition, McGraw Hili. ISBN 0-07-255642-0, Chapter 2: Bioenergetics, Chapter 10: Metabolic Response to Exercise: Lactate Metabolism During Exercise and Recovery, Excess Postexercise 02 Consumption (EPOC), 02 Deficit, 02 Debt, and the Anaerobic Threshold, Chapter 16: Cardiovascular Dynamics During Exercise, Chapter 2-1: Principles of Endurance Condifoning, Chapter 27: Exercise Testinc and Prescription, 141 pages (2004).

(56) References Cited

OTHER PUBLICATIONS

Bo et al, "TEXIVE: Detecting Drivers Using Personal Smart Phones by Leveraging Inertial Sensors," Department of Computer Science, Illinois Institute of Technology, Chicago IL, Dec. 7, 2014, pp. 1-12.
U.S. Appl. No. 15/692,726, Yet to Published, filed Aug. 31, 2017, Pending.
U.S. Appl. No. 15/692,237, Yet to Published, filed Aug. 31, 2017, Pending.
U.S. Appl. No. 15/692,736, Yet to Published, filed Aug. 31, 2017, Pending.
U.S. Appl. No. 15/691,245, Yet to Published, filed Aug. 30, 2017, Pending.
U.S. Appl. No. 15/689,113, Yet to Published, filed Aug. 29, 2017, Pending.
U.S. Appl. No. 15/679,538, Yet to Published, filed Aug. 17, 2017, Pending.
U.S. Appl. No. 15/678,645, Yet to Published, filed Aug. 16, 2017, Pending.
U.S. Appl. No. 15/616,135, Yet to Published, filed Jun. 7, 2017, Pending.
U.S. Appl. No. 15/611,010, Yet to Published, filed Jun. 1, 2017, Pending.
U.S. Appl. No. 15/273,054, 2017-0094450, filed Sep. 22, 2016, Published.
U.S. Appl. No. 15/273,038, 2017-0082649, filed Sep. 22, 2016, Published.
U.S. Appl. No. 15/264,976, 2017-0074897, filed Sep. 14, 2016, Published.
U.S. Appl. No. 15/061,653, 2016-0256058, filed Mar. 4, 2016, Published.
U.S. Appl. No. 14/501,930, 2016-0058329, filed Sep. 30, 2014, Issued.
U.S. Appl. No. 14/502,827, 2016-0058302, filed Sep. 30, 2014, Published.
U.S. Appl. No. 14/501,701, 2016-0058332, filed Sep. 30, 2014, Published.
U.S. Appl. No. 14/502,809, 2016-0058333, filed Sep. 30, 2014, Published.
U.S. Appl. No. 14/502,781, 2016-0058372, filed Sep. 30, 2014, Published.
U.S. Appl. No. 14/502,754, 2016-0058371, filed Sep. 30, 2014, Published.
U.S. Appl. No. 14/501,771, 2016-0058370, filed Sep. 30, 2014, Published.
U.S. Appl. No. 14/493,178, 2015-0087929, filed Sep. 22, 2014, Published.
U.S. Appl. No. 14/145,042, 2015-0088006, filed Dec. 31, 2013, Published.
U.S. Appl. No. 14/501,634, 2016-0058356, filed Sep. 30, 2014, Published.
U.S. Appl. No. 15/692,726, 2018-0056123, filed Aug. 31, 2017, Published.
U.S. Appl. No. 15/692,237, 2018-0056129, filed Aug. 31, 2017, Published.
U.S. Appl. No. 15/692,736, 2018-0055375, filed Aug. 31, 2017, Published.
U.S. Appl. No. 15/689,113, 2018-0055439, filed Aug. 29, 2017, Published.
U.S. Appl. No. 15/679,538, 2018-0050235, filed Aug. 17, 2017, Published.
U.S. Appl. No. 15/678,645, 2018-0049694, filed Aug. 16, 2017, Published.
U.S. Appl. No. 15/616,135, 2017-0347885, filed Jun. 7, 2017, Published.
U.S. Appl. No. 15/691,245, 2018-0056128, filed Aug. 30, 2017, Published.
U.S. Appl. No. 14/502,754, 2016-0058371, filed Sep. 30, 2014, Issued.
U.S. Appl. No. 14/493,178, 2015-0087929, filed Sep. 22, 2014, Abandoned.
Written Opinion from PCT/US2017/049693 dated Dec. 8, 2017.
International Search Report from PCT/US2017/049693 dated Dec. 8, 2017.
Novatel, "IMU Error and Their Effects", Novatel Application Notes, APN-064 Rev A, Feb. 21, 2014, pp. 1-6.
International Search Report and Written Opinion received for PCT Patent Application No. PCT/US2018/047290, dated Nov. 8, 2018, 14 pages.
Yamaji, et al (Relationship Between Heart Rate and Relative Oxygen Intake in Male Subjects Aged 10 to 27 Years, 1978, J. Human Ergol., 7:29-39) (Year: 1978).
Kyle, Chester R., "Reduction of Wind Resistance and Power Output of Racing Cyclists and Runners Travelling in Groups", Ergonomics, vol. 22, No. 4, 1979, pp. 387-397.
KINprof, "Predictive VO2max tests", Web Video, Available Online at <https://www.youtube.com/watch?v=_9e3HcYism8>, May 31, 2011, 1 page.
Abstract of IN 259/KOL/2015 published Dec. 18, 2015.

* cited by examiner

TECHNIQUES FOR JOINTLY CALIBRATING LOAD AND AEROBIC CAPACITY

CROSS-REFERENCE TO RELATED APPLICATION

This application claims priority to and the benefit of U.S. Provisional Patent Application No. 62/311,479, filed on Mar. 22, 2016, the disclosure of which is incorporated herein by reference in its entirety.

FIELD OF THE INVENTION

The present disclosure relates generally to improving metabolic equivalent (MET) prediction and tracking and, more particularly, to techniques for jointly calibrating load and $\dot{V}O_2$max.

BACKGROUND

An individual's health or fitness can be assessed from the perspective of energy expenditure over time. Two techniques for estimating energy expenditure, or calorie burn, are described in the art. The first is based on measuring the physiologic and metabolic responses to exercise, while the second is based on measuring the physical work the body performs moving a defined load, or resistance, through space.

Physiological estimates of energy expenditure are most commonly based on heart rate. During moderate to vigorous exercise, heart rate is correlated with energy expenditure. At a macroscopic level, an individual's heart rate indicates how quickly the individual's body is delivering oxygen to vital organs and tissues, which consume the oxygen through oxidative cellular metabolism. The heart pumps blood through the lungs, where red blood cells absorb oxygen from the lungs. This oxygen-rich blood returns to the heart, from which it is pumped through blood vessels that distribute the blood throughout the body to its organs and tissues. Tissues absorb oxygen carried by the blood and use the oxygen in chemical reactions of oxidative metabolism, also known as aerobic metabolism, to provide energy for biological functions.

The rate at which an individual body consumes oxygen at a given point in time is referred to as the volumetric flow of oxygen into the tissues of the body, also known as "oxygen exchange rate," "oxygen uptake rate," or simply $\dot{V}O_2$ (e.g., liters of oxygen per minute). Controlling for differences in body size, $\dot{V}O_2$ is often reported for a given individual in terms of oxygen volume at standard temperature and pressure per unit of time per unit of body mass (e.g., ml/kg/min).

Specifically, $\dot{V}O_2$ measures the overall rate at which the body is engaged in oxidative metabolism. $\dot{V}O_2$ during various physical activities—and, consequently, energy expenditure during those physical activities—varies from individual to individual. In a laboratory setting, it may be possible to use indirect calorimetry (e.g., with a face mask that measures the rate of oxygen consumption and rate of carbon dioxide production), to measure an individual's aerobic capacity, also known as maximum $\dot{V}O_2$, or simply "$\dot{V}O_2$max." $\dot{V}O_2$max is the highest rate of oxygen exchange that an individual can sustain.

In addition to $\dot{V}O_2$max, several other parameters are used to estimate an individual's energy expenditure at a given heart rate. Maximum heart rate ($HR_{max}$) and resting heart rate (RHR) are two such examples. An individual's heart rate generally will not exceed a maximum value, and, during exercise, the individual will reach this heart rate at their maximum energy output. Similarly, the resting heart rate is the value obtained when the user is completely at rest, and corresponds to an energy expenditure equal to that needed to sustain only basic physiological processes. Heart rates between RHR and $HR_{max}$ are achieved at energy expenditures between these two extremes.

Most forms of aerobic exercise involved the repetitive application of muscular forces against a combination of intrinsic or extrinsic resistance forces (collectively, the load). For example, running involves repetitive gait cycles in which physical work is performed to accelerate the legs/arms around their respective joints (intrinsic load) while also propelling the body's center of mass against the resistive forces of air drag and gravity (extrinsic load). An alternative method of measuring energy expenditure therefore involves measuring the rate at which physical work is performed against a known or implied load.

Since the two general methods of energy expenditure should be equal over sufficiently long time scales, combinations of the two methods can be used to calibrate an unknown parameter. For example, during outdoor running where work rate can be accurately measured and internal resistive forces assumed constant, heart rate measurements can be used to calibrate a user's unknown $\dot{V}O_2$max. Conversely, for user's with a known $\dot{V}O_2$max exercising against a variable resistance, work rate measurements may be used to infer the unknown load.

A problem with existing methods is that load and $\dot{V}O_2$max are never perfectly known; therefore, existing calibration methods introduce bias by ignoring the effect of uncertainty in the value of one assumed parameter on the estimation of the other parameter. In addition, the requirement that either load or $\dot{V}O_2$max be known in advance limits the application of these calibration methods to specific users and specific exercise scenarios.

SUMMARY

The present disclosure relates to methods and systems for jointly calibrating both a load of exercise and a user's $\dot{V}O_2$max, applicable to a broad range of exercising scenarios.

In some embodiments, a method for jointly calibrating both a load of exercise and a user's aerobic capacity can comprise determining a prior probability distribution of the load of exercise and a prior probability distribution of the user's aerobic capacity by a processor circuit of a device. The processor circuit may compute a joint prior probability of the load of exercise and the user's aerobic capacity based on the prior probability distribution of the load of exercise and the prior probability distribution of the user's aerobic capacity.

In some embodiments, the method can comprise measuring a time-stamped work rate by one or more motion sensors of the device. The method may comprise measuring a time stamped heart rate by one or more heart rate sensors of the device. The processor circuit may compute a joint likelihood of the load of exercise and the user's aerobic capacity based on the measured time-stamped work rate and the measured time-stamped heart rate.

In some embodiments, the processor circuit may combine the joint prior probability and the joint likelihood to produce a joint posterior probability. The processor circuit may determine a relationship relating the load of exercise and the user's aerobic capacity based on the joint posterior probability.

In some embodiments, the method may comprise determining an exercise type by the processor circuit. The processor circuit can use the exercise type to determine the prior probability distribution of the load of exercise. The processor circuit can represent the prior probability distribution of the load of exercise by a distribution with a normalized variance and a mean based off the exercise type.

In some embodiments, the method may comprise determining user biometrics by the processor circuit. The processor circuit can use the user biometrics to determine the prior probability distribution of the user's aerobic capacity. The processor circuit may represent the prior probability distribution of the user's aerobic capacity by a distribution with a normalized variance and a mean based off the user biometrics.

In some embodiments, the method may comprise determining a likelihood of an observation associated with the load of exercise and a likelihood of an observation associated with the user's aerobic capacity by the processor circuit. The processor circuit may compute the joint likelihood for the load of exercise and the user's aerobic capacity based on the likelihood of the observation associated with the load of exercise and the likelihood of the observation associated with the user's aerobic capacity. The processor circuit may determine the likelihood of the observation associated with the load of exercise by calculating a mean and a variance based on the time-stamped work rate.

In some embodiments, a system for jointly calibrating both a load of exercise and a user's aerobic capacity may comprise one or more motion sensors configured to execute instructions causing the one or more motion sensors to measure parameters used to generate a time-stamped work rate and one or more heart rate sensors configured to execute instructions causing the one or more heart rate sensors to measure a time-stamped heart rate. The system may comprise a processor circuit coupled to the one or more motion sensors and the one or more heart rate sensors and configured to execute instructions causing the processor circuit to determine a prior probability distribution of the load of exercise, determine a prior probability distribution of the user's aerobic capacity, and compute a joint prior probability of the load of exercise and the user's aerobic capacity based on the prior probability distribution of the load of exercise and the prior probability distribution of the user's aerobic capacity. The instructions may further cause the processor circuit to compute a joint likelihood of the load of exercise and the user's aerobic capacity based on the measured time-stamped work rate and the measured time-stamped heart rate, and combine the joint prior probability and the joint likelihood to produce a joint posterior probability. The instructions may further cause the processor circuit to determine a relationship relating the load of exercise and the user's aerobic capacity based on the joint posterior probability. The relationship may be linear in some embodiments, including some examples discussed herein. In other embodiments, the relationship may be a direct relationship that is not necessarily linear.

In some embodiments, a mobile device for jointly calibrating both a load of exercise and a user's aerobic capacity may comprise one or more motion sensors configured to execute instructions causing the one or more motion sensors to measure a time-stamped work rate and one or more heart rate sensors configured to execute instructions causing the one or more heart rate sensors to measure a time-stamped heart rate. The mobile device may comprise a processor circuit coupled to the one or more motion sensors and the one or more heart rate sensors and configured to execute instructions causing the processor circuit to determine a prior probability distribution of the load of exercise, determine a prior probability distribution of the user's aerobic capacity, and compute a joint prior probability of the load of exercise and the user's aerobic capacity based on the prior probability distribution of the load of exercise and the prior probability distribution of the user's aerobic capacity. The instructions may further cause the processor circuit to compute a joint likelihood of the load of exercise and the user's aerobic capacity based on the measured time-stamped work rate and the measured time-stamped heart rate, and combine the joint prior probability and the joint likelihood to produce a joint posterior probability. The instructions may further cause the processor circuit to determine a relationship relating the load of exercise and the user's aerobic capacity based on the joint posterior probability.

Other features and advantages will become apparent from the following detailed description and drawings.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

DETAILED DESCRIPTION

There is growing interest to assess and monitor one's health or fitness and physical activity. The present disclosure describes a fitness tracking device that may be configured to provide an accurate, individualized quantification of load and $\dot{V}O_2$max over time and across a variety of activities. The device may implement sophisticated calorimetry techniques based on empirical models and sophisticated algorithms that may use motion data, heart rate data, or a weighted combination of both motion data and heart rate data.

Fitness Tracking Devices

Figure 1:
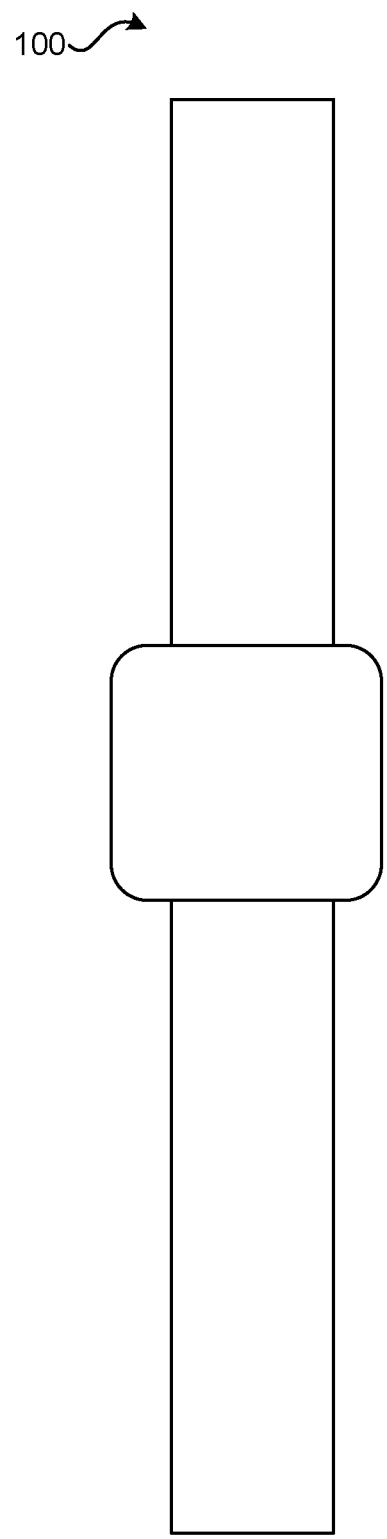
FIG. 1 shows a fitness tracking device in accordance with an embodiment of the present disclosure.

FIG. 1 shows an example of a fitness tracking device 100 in accordance with an embodiment of the present disclosure. In some embodiments, the fitness tracking device 100 may be a wearable device, such as a watch configured to be worn around an individual's wrist. As described in more detail below, the fitness tracking device 100 may be calibrated according to physical attributes of the individual and physical activity by the individual user who is wearing the fitness tracking device 100, including, for example, heart rate statistics, steps counts, or frequency of exercise.

Figure 2:
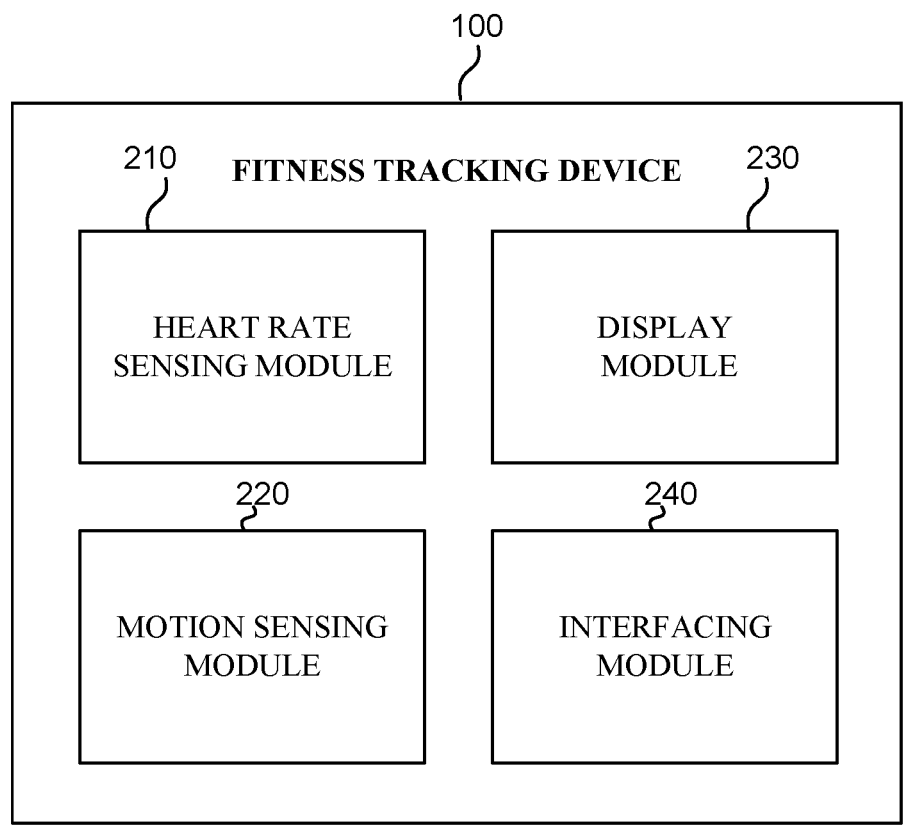
FIG. 2 depicts a block diagram of a fitness tracking device in accordance with an embodiment of the present disclosure.

FIG. 2 depicts a block diagram of example components that may be found within the fitness tracking device 100 in accordance with an embodiment of the present disclosure. These components may include a heart rate sensing module 210, a motion sensing module 220, a display module 230, and an interface module 240.

The heart rate sensing module 210 may include or may be in communication with a photoplethysmogram "PPG" sensor. The fitness tracking device 100 can measure an individual's current heart rate from the PPG. The heart rate sensor may also be configured to determine a confidence level indicating a relative likelihood of an accuracy of a given heart rate measurement. In other embodiments, a traditional heart rate monitor may be used and may communicate with the fitness tracking device 100 through a near field communication method (e.g., Bluetooth). In some embodiments, the heart rate sensor can include or be operably connected to a timing device, such that the measured heart rate values are time-stamped.

The fitness tracking device 100 may include an LED and a photodiode or the equivalent to obtain a PPG. The fitness tracking device 100 may subsequently determine the user's current heart rate based on the PPG data.

To conserve battery power on the fitness tracking device 100, the LED may be a relatively low-power LED, such as a green LED. In some embodiments, to further conserve power on the fitness tracking device 100, the fitness tracking device 100 may be configured to check heart rate at periodic intervals (e.g., once per minute, or once per three minutes). The period for checking heart rate may change dynamically. For example, if the fitness tracking device 100 automatically detects or receives input from the user that the user is engaged in a certain level, intensity, or type of physical activity (e.g., "in session"), the fitness tracking device may check heart rate more frequently (e.g., once per five seconds, once per minute, etc.). The fitness tracking device 100 may use, for example, machine learning techniques, battery power monitoring, or physical activity monitoring to balance the frequency of heart rate samples for accurate calorimetry with power optimization.

In addition to the heart rate sensing module 210, the fitness tracking device 100 may also include the motion sensing module 220. The motion sensing module 220 may include one or more motion sensors, such as an accelerometer or a gyroscope. In some embodiments, the accelerometer may be a three-axis, microelectromechanical system (MEMS) accelerometer, and the gyroscope may be a three-axis MEMS gyroscope. A microprocessor (not shown) or motion coprocessor (not shown) of the fitness tracking device 100 may receive motion information from the motion sensors of the motion sensing module 220 to track acceleration, rotation, position, or orientation information of the fitness tracking device 100 in six degrees of freedom through three-dimensional space.

In some embodiments, the motion sensing module 220 may include other types of sensors in addition to accelerometers and gyroscopes. For example, the motion sensing module 220 may include an altimeter or barometer, or other types of location sensors, such as a GPS sensor.

In some embodiments, the fitness tracking device 100 may take advantage of the knowledge that the heart rate sensing module 210 and the motion sensing module 220 are approximately co-located in space and time to combine data from each module 210 and 220 to improve the accuracy of its calorimetry functionality. Depending on the current activity and a determination of a confidence of current heart rate and motion data, the fitness tracking device 100 may also rely on one, or a combination, of a heart rate or a motion-derived work rate to estimate energy expenditure more accurately.

The fitness tracking device 100 may also include a display module 230. Display module 230 may be a screen, such as a crystalline (e.g., sapphire) or glass touchscreen, configured to provide output to the user as well as receive input form the user via touch. For example, display 230 may be configured to display a current heart rate or a daily average energy expenditure. Display module 230 may receive input from the user to select, for example, which information should be displayed, or whether the user is beginning a physical activity (e.g., starting a session) or ending a physical activity (e.g., ending a session), such as a running session or a cycling session. In some embodiments, the fitness tracking device 100 may present output to the user in other ways, such as by producing sound with a speaker (not shown), and the fitness tracking device 100 may receive input from the user in other ways, such as by receiving voice commands via a microphone (not shown).

In some embodiments, the fitness tracking device 100 may communicate with external devices via interface module 240, including a configuration to present output to a user or receive input from a user. Interface module 240 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as LTE or a Wi-Fi (IEEE 802.11) protocol. In other embodiments, interface module 240 may include wired interfaces, such as a headphone jack or bus connector (e.g., Lightning, Thunderbolt, USB, etc.).

The fitness tracking device 100 may be configured to communicate with a companion device 300 (FIG. 3), such as a smartphone, as described in more detail herein. In some embodiments, the fitness tracking device 100 may be configured to communicate with other external devices, such as a notebook or desktop computer, tablet, headphones, Bluetooth headset, etc.

The modules described above are examples, and embodiments of the fitness tracking device 100 may include other modules not shown. For example, the fitness tracking device 100 may include one or more microprocessors (not shown) for processing heart rate data, motion data, other information in the fitness tracking device 100, or executing instructions for firmware or apps stored in a non-transitory processor-readable medium such as a memory module (not shown). Additionally, some embodiments of the fitness tracking device 100 may include a rechargeable battery (e.g., a lithium-ion battery), a microphone or a microphone array, one or more cameras, one or more speakers, a watchband, a crystalline (e.g., sapphire) or glass-covered scratch-resistant display, water-resistant casing or coating, etc.

Figure 3:
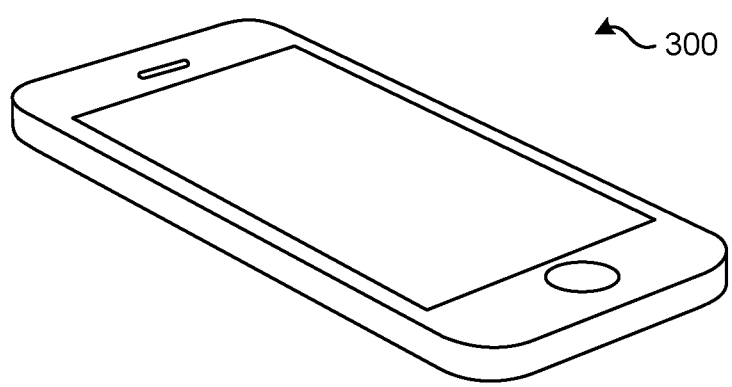
FIG. 3 shows a companion device in accordance with an embodiment of the present disclosure.

FIG. 3 shows an example of a companion device 300 in accordance with an embodiment of the present disclosure. The fitness tracking device 100 may be configured to communicate with the companion device 300 via a wired or wireless communication channel (e.g., Bluetooth, Wi-Fi, etc.). In some embodiments, the companion device 300 may be a smartphone, tablet, or similar portable computing device. The companion device 300 may be carried by the user, stored in the user's pocket, strapped to the user's arm with an armband or similar device, placed on a table, or otherwise positioned within communicable range of the fitness tracking device 100.

The companion device 300 may include a variety of sensors, such as location and motion sensors (not shown). When the companion device 300 may be optionally available for communication with the fitness tracking device 100, the fitness tracking device 100 may receive additional data from the companion device 300 to improve or supplement its calibration or calorimetry processes. For example, in some embodiments, the fitness tracking device 100 may not include a GPS sensor as opposed to an alternative embodiment in which the fitness tracking device 100 may include a GPS sensor. In the case where the fitness tracking device 100 may not include a GPS sensor, a GPS sensor of the companion device 300 may collect GPS location information, and the fitness tracking device 100 may receive the GPS location information via interface module 240 (FIG. 2) from the companion device 300.

In another example, the fitness tracking device 100 may not include an altimeter, as opposed to an alternative embodiment in which the fitness tracking device 100 may include an altimeter. In the case where the fitness tracking device 100 may not include an altimeter or barometer, an altimeter or barometer of the companion device 300 may collect altitude or relative altitude information, and the fitness tracking device 100 may receive the altitude or relative altitude information via interface module 240 (FIG. 2) from the companion device 300.

In some embodiments, exercise type and user biometrics can be received by either the fitness tracking device 100 or the companion device 300. Exercise type can refer to any form of aerobic activity, including but not limited to running, walking, biking, swimming, dancing, etc. User biometrics can include a user's age, gender, height, and weight. In some embodiments, the fitness tracking device 100 may determine the user's age based on the user's birthday or birth year in comparison to a current date or year. As time passes and the user ages, the fitness tracking device 100 may automatically increase the age value at input and may automatically estimate a new $HR_{max}$ for the user. Gender, height, and weight may be inputted manually by the user or obtained from external sensors or databases, such as a wireless-enabled scale or an electronic health record. The fitness tracking device 100 and the companion device 300 can receive the exercise type and user biometrics by at least one of user input through interface module 240, or from a database attached locally or through a communications channel. Biometrics can also be added from the companion device.

Heart Rate-Based Determination of Energy Expenditure

As explained in more detail below with respect to FIGS. 4-7, measured heart rate, as well as user biometrics, can be used to determine $\dot{V}O_2$max, and subsequently energy expenditure (also referred to herein as METs).

For example, and as explained above, an individual exhibits a correlation between heart rate (varying between the individual's resting heart rate RHR and maximum heart rate $HR_{max}$) and $\dot{V}O_2$ (up to the individual's aerobic capacity, or $\dot{V}O_2$max). Thus, there is also a correlation between heart rate and energy expenditure. Additionally, $\dot{V}O_2$ is linked to a user's aerobic power output based on the user's metabolic rate, which may also vary from one individual to the next. Metabolic rate may be expressed in Metabolic Equivalents of Task, or METs. METs indicates how many calories a "typical" individual burns per unit of body mass per unit of time. An individual's RHR is also referred to herein as a minimum heart rate $HR_{min}$. Resting heart rate is the heart rate obtained in a specific resting protocol, while the minimum heart rate is the minimum heart rate observed. Except for disease states (such as abnormal heart rhythms), these can safely assumed to be equal.

If the user's weight is known, and the user undergoes testing to measure the user's maximum heart rate and $\dot{V}O_2$max, a device may be able to construct an individualized model of energy expenditure for a given heart rate.

In situations such as laboratory testing, it may be possible to test and measure a user's $\dot{V}O_2$max and maximum heart rate ("$HR_{max}$"). With these predetermined values, a device may be able to estimate energy expenditure more accurately based on a user's current heart rate during moderate to high-intensity physical activity or exercise. Without laboratory testing (e.g., testing based on indirect calorimetry), $\dot{V}O_2$max and $HR_{max}$ may be estimated with other methods, such as submaximal exercise testing or non-exercise testing. For example, $HR_{max}$ may be estimated based on the user's age. In some embodiments, if a heart rate greater than the age-predicted $HR_{max}$ is observed, then the device may update the estimate of $HR_{max}$ to use the higher, observed heart rate. In some embodiments, the device may determine whether to use an age-based estimate or a higher observed heart rate based on a confidence level for the heart rate measurement or whether the higher observed heart rate was sustained for a threshold period of time.

An individual's current heart rate (HR) as it compares to the range of an individual's heart rate from resting heart rate RHR (e.g., $HR_{min}$, or $HR_{onset}$) and maximum heart rate $HR_{max}$ may be expressed as a value called "Fraction of Heart Rate Reserve" (FHR):

$$FHR=(HR_{max}-HR)/(HR_{max}-RHR) \quad \text{(Eq. 1)}$$

FHR may range from 0 to 1 for any individual. When an individual's FHR is close to 0, it indicates that the user's heart rate HR is close to the individual's maximum heart rate. Similarly, when an individual's FHR is close to 1, it indicates that the individual's heart rate is close to the individual's resting heart rate (e.g., $HR_{min}$ or $HR_{onset}$). Thus, for example, if the individual's FHR is less than 0.5, the user's heart rate is closer to maximum heart rate than to resting heart rate.

One method of determining energy expenditure (EE) may be determined using a calorimetry model with a parameterized function of FHR:

$$EE=\dot{V}O_2\text{max}\cdot f(FHR) \quad \text{(Eq. 2)}$$

The function $f(FHR)$ may be an approximately sigmoidal nonlinearity. When FHR=0, $f(0)$ may equal 1. $f(1)$ may equal 0, or a fractional margin above 0 (e.g., approximately 0.1, 0.2, or 0.3). The slope of the function $f(FHR)$ may be approximately 1 (i.e., the "unity" slope) for a range of FHR, such as when FHR=[0, 0.5], or FHR=[0, 0.6]. In other embodiments, other definitions for f(FHR) may be used, including other minimum and maximum values, or other slopes, including other regions or ranges of FHR for which the function's slope equals 1 or approximately 1.

The user's resting heart rate (RHR), which, in some embodiments, may be represented as the user's minimum heart rate ($HR_{min}$ or $HR_0$) may be observed by the device as well or adjusted if even lower measurements are observed. In some embodiments, RHR may be represented by the user's heart rate at the onset of an exercise session ($HR_{onset}$), which may be higher than the user's $HR_{min}$ under certain circumstances, such as when the user has recently finished a prior exercise session. In some instances, as described in greater detail below, the calorimetry model may be more accurate when $HR_{onset}$ is used as the value of the RHR parameter instead of $HR_{min}$.

Figure 4:
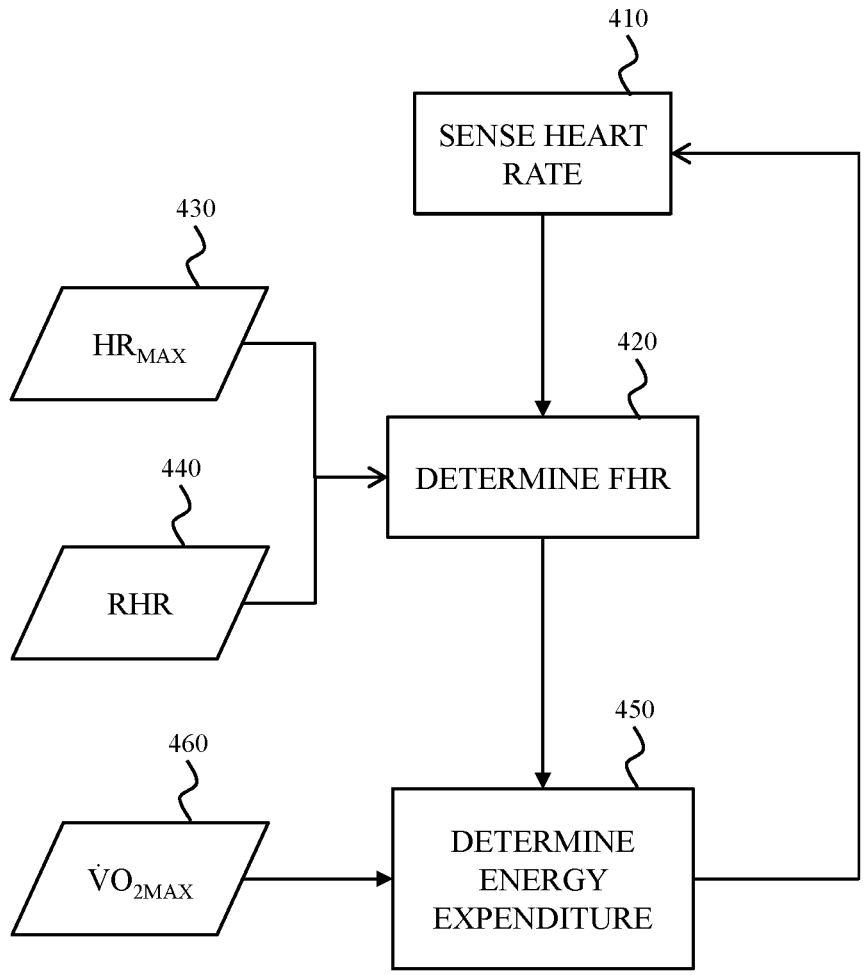
FIG. 4 shows a calorimetry method in accordance with an embodiment of the present disclosure.

FIG. 4 shows a calorimetry method 400 using VO2max and heart rate, in accordance with an embodiment of the present disclosure. Fitness tracking device 100, companion device 300, or a combination thereof may perform calorimetry method 400. In the following example, fitness tracking device 100 performs the method. Calorimetry method 400 may begin at block 410.

At block 410, fitness tracking device 100 may sense the user's current heart rate (HR). In some embodiments, the user's heart rate may be sensed using the heart rate sensing module 210 of the fitness tracking device 100. The user's heart rate may be provided as input to block 420.

At block 420, fitness tracking device 100 may determine the user's current Fraction of Heart Rate Reserve (FHR). In some embodiments, the user's current FHR may be determined according to Eq. 1, which is a function of heart rate (HR), parameterized by $HR_{max}$ and RHR. In some embodiments, the value of the $HR_{max}$ parameter may be provided by $HR_{max}$ input 430, and the value of the RHR parameter may be provided by RHR input 440. Inputs 430 and 440 may be retrieved from a memory of the fitness tracking device 100. Inputs 430 and 440 may be represented by default values or values that were previously calibrated for the user using various techniques described herein. In some embodiments, one or more of inputs 430 and 440 may be measured, calibrated, or otherwise determined during the execution of calorimetry method 400. The user's FHR may be provided as input to block 450.

At block 450, fitness tracking device 100 may determine the user's current rate of energy expenditure. In some embodiments, the user's current rate of energy expenditure may be determined by a calorimetry model according to Eq. 2, which is a function of FHR, parameterized by $VO_2max$. In some embodiments, the value of the $VO_2max$ parameter may be provided by $VO_2max$ input 460. Input 460 may be represented by a default value or a value that was previously calibrated for the user. The determined rate of energy expenditure may be stored in a memory of the fitness tracking device 100, output to another process, or otherwise aggregated within calorimetry method 400.

In some embodiments, calorimetry method 400 may return to block 410, repeating the determination of energy expenditure for the user's current heart rate at subsequent points in time until the user or another process of the fitness tracking device 100 halts or pauses calorimetry method 400.

Figure 5:
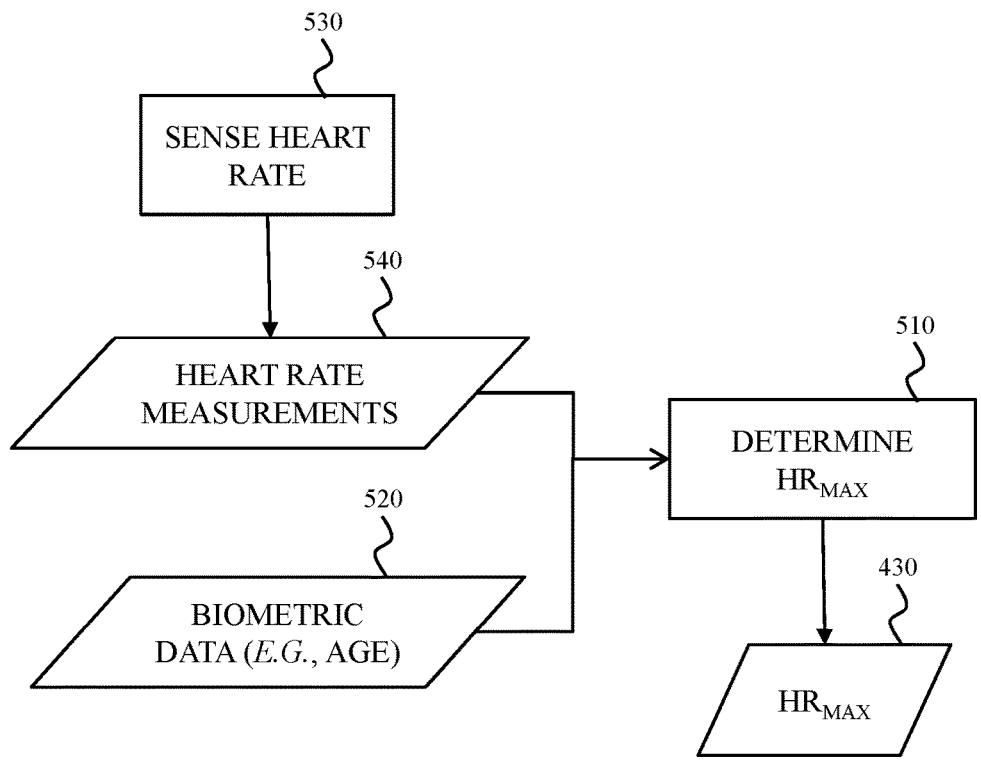
FIG. 5 depicts a calibration method for determining a value for the $HR_{max}$ parameter in accordance with an embodiment of the present disclosure.
Figure 6:
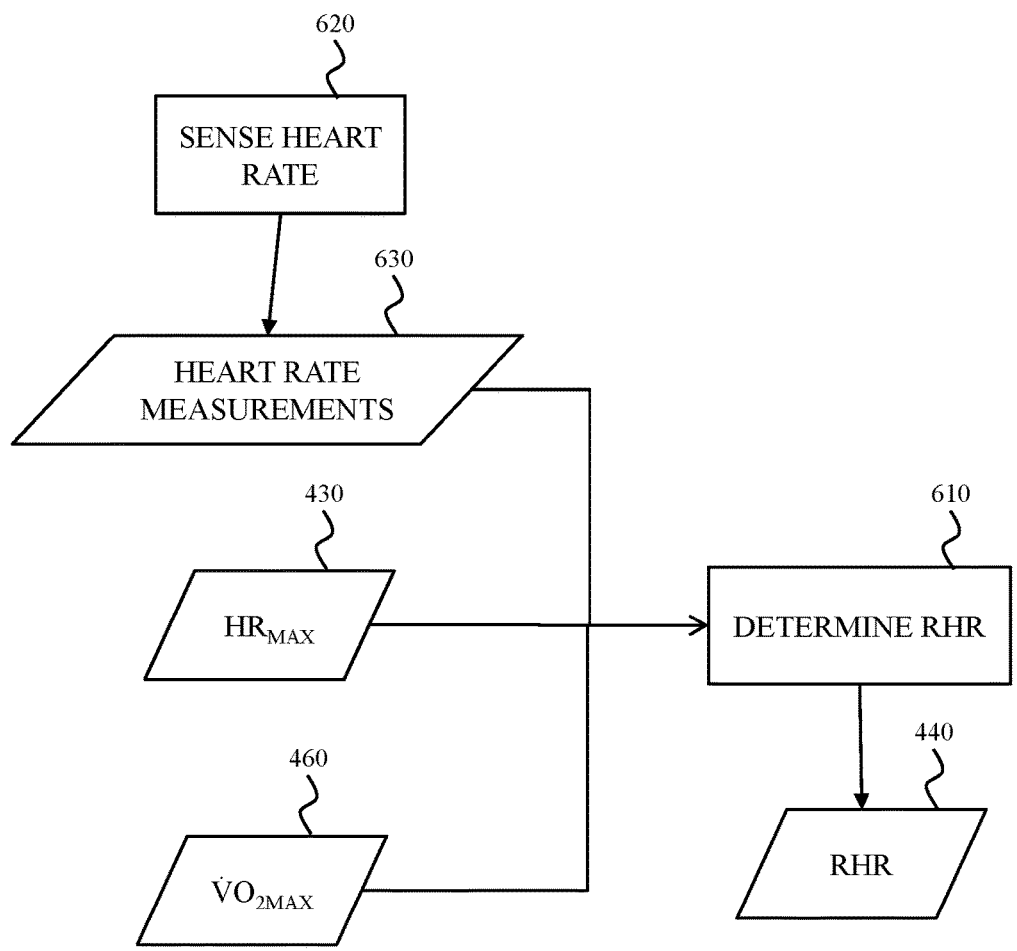
FIG. 6 shows a calibration method for determining a value for the RHR parameter in accordance with an embodiment of the present disclosure.
Figure 7:
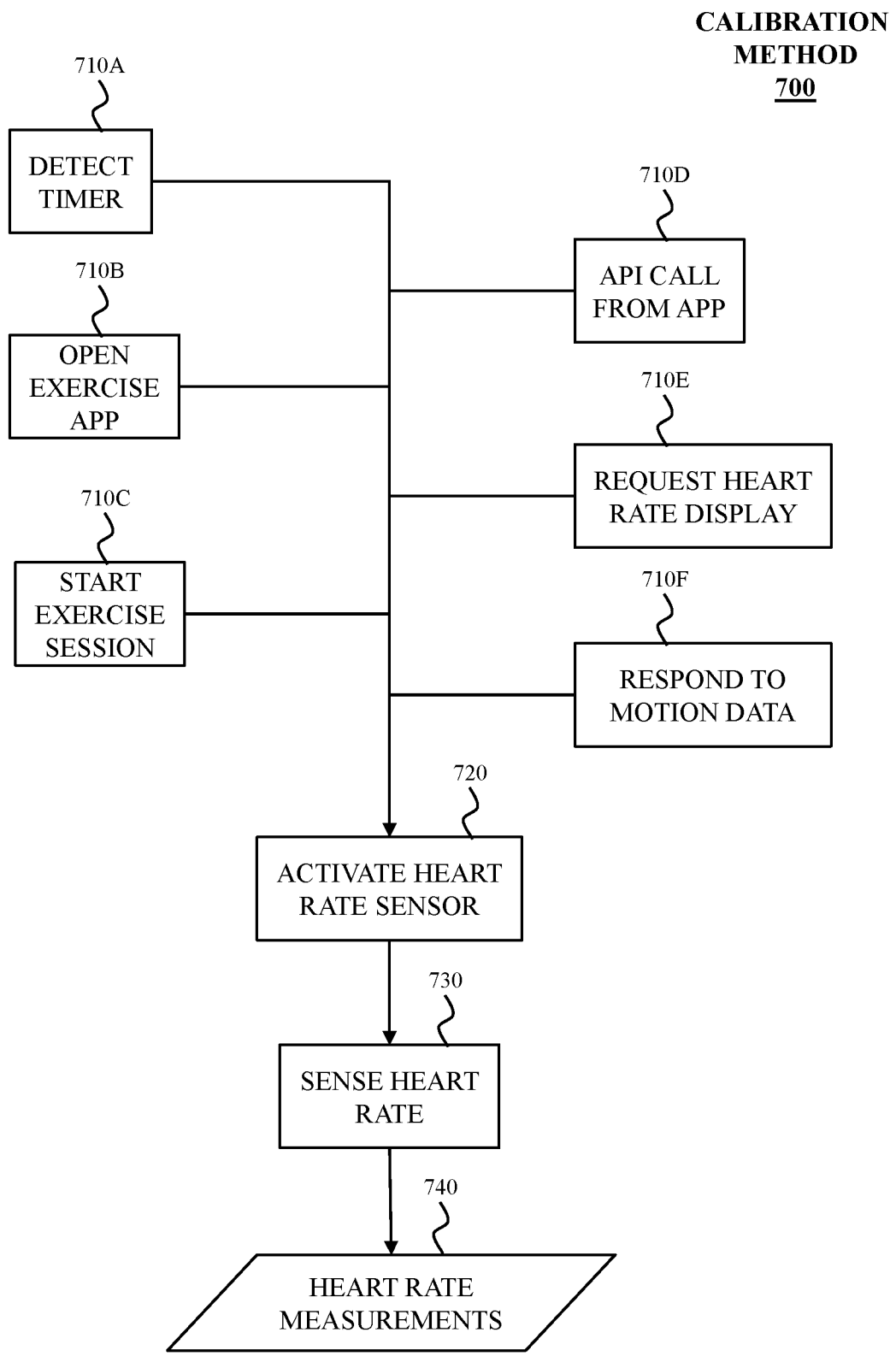
FIG. 7 shows a calibration method for collecting heart rate measurements in accordance with an embodiment of the present disclosure.

FIGS. 5 and 6 depict methods for determining values for $HR_{max}$ and $HR_{min}$ that can be used in methods depicted in FIG. 4, FIG. 6, and FIG. 7. Fitness tracking device 100, companion device 300, or a combination thereof may perform methods depicted in FIG. 4, FIG. 6, and FIG. 7. In the following examples, fitness tracking device 100 performs the methods.

FIG. 5 depicts a calibration method 500 for determining a value for the $HR_{max}$ parameter in accordance with an embodiment of the present disclosure. The calibration method 500 may begin at block 510.

At block 510, fitness tracking device 100 may determine a value for the user's $HR_{max}$. In some embodiments, the user's $HR_{max}$ may be determined according to the following equation (Eq. 3):

$$HR_{max}=A-B(\text{age}) \quad \text{(Eq. 3)}$$

Eq. 3 describes the inverse relationship between a user's maximum heart rate $HR_{max}$ and the user's age—as the user gets older, the user's maximum heart rate decreases. Fitness tracking device 100 may select values for constants A and B in Eq. 3 to estimate the user's $HR_{max}$. For example, A may equal 200, or 205, or 210, etc., and B may equal 0.9, 0.8, 0.7, etc.

Fitness tracking device 100 may receive biometric data about the user at input 520. In some embodiments, biometric data may include the user's age. In some embodiments, the fitness tracking device 100 may determine the user's age based on the user's birthday or birth year in comparison to a current date or year. As time passes and the user ages, the fitness tracking device 100 may automatically increase the age value at input 520 and may automatically determine a new $HR_{max}$ for the user.

In some embodiments, fitness tracking device 100 may determine the user's $HR_{max}$ using previously measured heart rate measurements 540. The previously measured heart rate measurements may have been previously sensed at 530 using the heart rate sensing module 210 of the fitness tracking device 100.

The heart rate measurements 540 may be used in a variety of techniques to predict or help predict the user's $HR_{max}$. For example, in some embodiments, the fitness tracking device 100 may compile a list of heart rate measurements 540 and apply a statistical function (or "statistical estimator") to select, compute, or otherwise determine a value to use as $HR_{max}$. For example, block 510 (or another process of the fitness tracking device 100) may select the maximum value from the heart rate measurements to use as $HR_{max}$.

Another example of a statistical estimator for $HR_{max}$ may be to determine a percentile (e.g., the 95th percentile, or the 98th percentile), of all of the heart rate measurements.

Yet another statistical estimator for $HR_{max}$ may be to determine a percentile (e.g., the 95th percentile, or the 98th percentile), of all of the heart rate measurements that were above a cutoff value (e.g., 100 beats per minute, or 150 beats per minute, etc.), if any.

Yet another statistical estimator for $HR_{max}$ may be to determine a percentile (e.g., the 95th percentile, or the 98th percentile), of all of the heart rate measurements that were above a threshold fraction of the user's $HR_{max}$ as determined based on the user's age (e.g., measurements above 85% of the age-based $HR_{max}$, or above 90% of the age-based $HR_{max}$, etc.), if any. In some embodiments, this statistical estimator may establish a lower bound on observed $HR_{max}$ using the age-based $HR_{max}$.

Yet another statistical estimator for $HR_{max}$ may be to determine a percentile (e.g., the 95th percentile, or the 98th percentile), of all of the heart rate measurements that were below a threshold fraction of the user's $HR_{max}$ as determined based on the user's age (e.g., measurements below 110% of the age-based $HR_{max}$, or below 115% of the age-based $HR_{max}$, etc.), if any. In some embodiments, this statistical estimator may establish an upper bound on observed $HR_{max}$ using the age-based $HR_{max}$.

Yet another statistical estimator for $HR_{max}$ may take into account both a lower bound and an upper bound on observed $HR_{max}$ using the age-based $HR_{max}$, such as using the lower-bound and upper-bound techniques described above.

In some embodiments, fitness tracking device 100 may determine $HR_{max}$ using either the user's biometric data at input 520 or the user's heart rate measurements at input 540, or a combination of both inputs 520 and 540. The value of $HR_{max}$ determined at block 510 may be stored, transmitted, or otherwise used as the $HR_{max}$ parameter 430 in calorimetry method 400.

FIG. 6 shows a calibration method 600 for determining a value for the RHR parameter in accordance with an embodiment of the present disclosure. The calibration method 600 may begin at block 610.

At block 610, fitness tracking device 100 may determine a value for the user's RHR. In some embodiments, RHR may be set to a default value (e.g., 70 beats per minute, 72 beats per minute, 75 beats per minute, etc.)

In some embodiments, the user's RHR may be determined according to the following equation (Eq. 4):

$$RHR = A \cdot HR_{max} / \dot{V}O_2 max \qquad \text{(Eq. 4)}$$

Eq. 4 describes the relationship between a user's resting heart rate (RHR) and some of the user's other biometrics, i.e., the user's maximum heart rate ($HR_{max}$) and the user's maximum rate of oxygen exchange ($\dot{V}O_2 max$). Eq. 4 predicts that a user with a relatively low ratio of $HR_{max}$ to $\dot{V}O_2 max$ may have a relatively lower RHR as well. Eq. 4 includes a scaling parameter (A) to convert the ratio of $HR_{max}$ to $\dot{V}O_2 max$ into an estimate of RHR in beats per minute. The scaling parameter in Eq. 4 (A) may be fixed or otherwise determined. In some embodiments, the scaling parameter (A) may equal, for example, approximately 10, 15, 20, etc.

In some embodiments, fitness tracking device 100 may receive $HR_{max}$ parameter 430 and $\dot{V}O_2 max$ parameter 460 as inputs at block 610 so that RHR may be determined based on these values using, for example, the technique based on Eq. 4.

In some embodiments, fitness tracking device 100 may determine the user's RHR using heart rate measurements 630. Fitness tracking device 100 may have previously sensed the heart rate measurements at 620 using the heart rate sensing module 210 of fitness tracking device 100. In some embodiments, the heart rate measurements 630 used to determine RHR may include the heart rate measurements 540 used to determine $HR_{max}$. In other embodiments, some or all of the heart rate measurements 630 for RHR may have been collected separately from the heart rate measurements 540 for $HR_{max}$.

In some embodiments, fitness tracking device 100 may determine RHR to be the lowest value determined by any of the previously described methods such as the default value (e.g., 70 beats per minute), the value based on the user's biometrics, or one or more of the values determined using heart rate measurements. The value of RHR determined at block 610 may be stored, transmitted, or otherwise used as the RHR parameter 440 in calorimetry method 400.

The heart rate measurements 630 may be used in a variety of techniques to predict or help predict the user's RHR. For example, in some embodiments, the fitness tracking device 100 may compile a list of heart rate measurements 630 and apply a statistical estimator to select, compute, or otherwise determine a value to use as RHR. For example, block 610 (or another process of the fitness tracking device 100) may select the minimum value from the heart rate measurements to use as RHR. This minimum value may also be referred to as the user's minimum heart rate, $HR_{min}$.

Another example of a statistical estimator for RHR may be to determine a percentile (e.g., the 95th percentile, or the 98th percentile), of all of the heart rate measurements.

Yet another statistical estimator for RHR may be to determine a percentile (e.g., the 95th percentile, or the 98th percentile), of all of the heart rate measurements that were above a cutoff value (e.g., 60 beats per minute, or 70 beats per minute, etc.), if any.

Yet another statistical estimator for RHR may be to determine a percentile (e.g., the 95th percentile, or the 98th percentile), of all of the heart rate measurements that were above a cutoff value (e.g., 60 beats per minute, or 70 beats per minute, etc.), if any.

Yet another statistical estimator for RHR may be to determine a percentile (e.g., the 95th percentile, or the 98th percentile), of all of the heart rate measurements that were below a cutoff value (e.g., 100 beats per minute, or 90 beats per minute, etc.), if any.

Yet another statistical estimator for RHR may take into account both a lower bound and an upper bound on $HR_{onset}$, such as by using a combination of the lower-bound and upper-bound techniques described above.

In some embodiments, the fitness tracking device 100 may enable collection (e.g., sensing) of heart rate measurements during a first portion of an exercise session. For example, when a user indicates that the user is starting an exercise session (e.g., via an interactive application running on the fitness tracking device 100), or when the fitness tracking device 100 detects the beginning of an exercise session (e.g., based on heart rate dynamics or motion data), the fitness tracking device 100 may record or otherwise add subsequent heart rate measurements to the heart rate measurements 630 for a period of time (e.g., for 10 seconds, 20 seconds, 30 seconds, one minute, etc.). Fitness tracking device 100 may select the minimum value from—or apply a different statistical estimator to—this set of heart rate measurements to use at RHR (e.g., at block 610). For these embodiments, the minimum value may also be referred to the heart rate at the onset of exercise ($HR_{onset}$).

In some situations, a user's $HR_{onset}$ measured around the time of the beginning of an exercise session, may be higher than the user's $HR_{min}$. For example, if the user had recently exercised earlier in the day, the user's heart rate may not have returned to the user's minimum (resting) heart rate (during a "cool down" period). Instead, $HR_{onset}$ may account for a higher heart rate at the beginning of an exercise session.

In some embodiments, fitness tracking device 100 may compute $HR_{onset}$ during a period of time before the beginning of an exercise session. For example, the fitness tracking device 100 may determine that a user is about to begin an exercise session when the user opens a fitness tracking application. The fitness tracking device 100 may sense or otherwise collect heart rate measurements 630 for a period of time between the user activating the application and subsequently indicating within the application that the user is beginning an exercise session. In some embodiments, some of the heart rate measurements 630 may be collected prior to beginning an exercise session, and some of the heart rate measurements 630 may be collected after beginning the exercise session.

In some embodiments, fitness tracking device 100 may determine $HR_{onset}$ by, for example, selecting the minimum value, or by computing the second percentile, of heart rate measurements collected prior to an exercise session (e.g., 5 minutes, 10 minutes, 15 minutes, 30 minutes, one hour, etc. prior to beginning an exercise session).

In some embodiments, fitness tracking device 100 may determine $HR_{onset}$ by, for example, selecting the minimum value, or by computing a percentile, of heart rate measurements collected for a period of time (e.g., 30 minutes, 60 minutes, etc.) ending before the exercise session begins (e.g., ending 10 minutes, 15 minutes, etc. before the exercise session begins).

In some embodiments, fitness tracking device 100 may determine $HR_{onset}$ using weighted sums of heart rate measurements from a period of time, such as a period of time 45 minutes or 60 minutes before the exercise session begins. For example, the weights may be based on the value of the heart rate measurement relative to a fixed value, or relative to other heart rate measurements collected during this period of time. For another example, the weights may be based on the time each heart measurement is taken relative to the time that the exercise session begins. For yet another example, the weights may be based on a combination of the value of the heart rate measurement and the time at which the heart rate measurement was taken.

Fitness tracking device 100 may output a value for the RHR parameter 440 (e.g., a default RHR, or a statistically determined value for $HR_{min}$ or $HR_{onset}$) at block 510. In some embodiments, fitness tracking device 100 using the calorimetry method 400 (FIG. 4) may be able to determine energy expenditure more accurately if the RHR parameter 440 is the user's $HR_{onset}$ instead of the user's $HR_{min}$. In these embodiments, fitness tracking device 100 may determine the user's onset heart rate ($HR_{onset}$) and output that value as RHR parameter 440 (e.g., at block 610). If $HR_{onset}$ cannot be obtained, or if the obtained $HR_{onset}$ value is determined to be inaccurate, fitness tracking device 100 may output the user's $HR_{min}$ value as the RHR parameter 440 instead (e.g., at block 510).

FIG. 7 shows a calibration method 700 for collecting heart rate measurements in accordance with an embodiment of the present disclosure. Several techniques for determining biometric parameters for estimating energy expenditure (e.g., $HR_{max}$, RHR, etc.) include collecting heart rate measurements using a heart rate sensor such as heart rate sensing module 210 in fitness tracking device 100. For example, heart rate measurements 540 (FIG. 5) may be collected to determine $HR_{max}$, and heart rate measurements 630 (FIG. 6) may be collected to determine RHR (e.g., $HR_{min}$ or $HR_{onset}$).

Calibration method 700 generally begins when an event occurs that requires or otherwise requests heart rate measurements. Examples of these events are represented as parts of blocks 710A-710F. Calibration method 700 may begin at any block 710A-710F depending on which event may be driving the request for heart rate measurements, and then proceed to block 720.

In some embodiments, fitness tracking device 100, using calibration method 700, may define events specially or exclusively for the purpose of calibrating one or more parameters to use for estimating energy expenditure. In some embodiments described in detail below, fitness tracking device 100, using calibration method 700, may opportunistically collect heart rate measurements for parameter calibration following events when the heart rate sensor needed to be activated for a different process.

At block 710A, calibration method 700 may begin with a timer event. For example, as described above in relation to collecting heart rate measurements for $HR_{onset}$, a timer may be used to determine when the heart rate sensor should be activated (at block 720).

In other embodiments, other processes of the fitness tracking device 100 or applications running on the fitness tracking device 100 may define a timer event (block 710A). For example, the fitness tracking device 100 may define a timer event that triggers periodically to collect heart rate measurements at regular intervals throughout the day. For example, the timer may be defined to have a period of 10 minutes, 30 minutes, 1 hour, etc.

In some embodiments, this timer may activate a "low-power" mode of the heart rate sensor (e.g., heart rate sensing module 210) at block 720. The low-power mode may use fewer elements (e.g., two LEDs instead of four), or the low-power mode may use lower-power elements (e.g., infrared LEDs instead of colored LEDs). When the heart rate is sensed at block 730 or when the heart rate measurement is collected at output 740, fitness tracking device 100 may take into account whether the heart rate sensing module is operating in a low-power mode. For example, heart rate measurements taken in low-power mode may be less accurate than heart rate measurements taken in a higher-power mode (or a "normal" mode).

In some embodiments, calibration method 700 may begin at block 710B. The fitness tracking device 100 may be configured with a built-in exercise or fitness application. When this app is "opened" or otherwise run, launched, executed, or resumed, the fitness tracking device 100 may proceed to activate the heart rate sensor at block 720 and sense the user's heart rate at block 730. Fitness tracking device 100 may opportunistically collect these heart rate measurements to be used for determining parameters used for estimating energy expenditure.

In some embodiments, calibration method 700 may begin at block 710C. A fitness application (e.g., the built-in exercise application) may signal that the user indicated the start or beginning of an exercise session. This signal may cause the fitness tracking device 100 to proceed to activate the heart rate sensor at block 720 and sense the user's heart rate at block 730. Fitness tracking device 100 may opportunistically collect these heart rate measurements to be used for determining parameters used for estimating energy expenditure.

In some embodiments, calibration method 700 may begin at block 710D. Third-party applications (or "apps") may be downloaded, installed, transferred, or otherwise configured to run on the fitness tracking device. The fitness tracking device 100 may provide an application programming interface (API) or other hook or process within its processor, firmware, operating system, or other built-in software libraries for a third-party application to request heart rate data or information depending on heart rate data. For example, a third-party exercise app may include a "start" function that allows the user to signal the beginning of an exercise session within the third-party exercise app. This signal may cause the fitness tracking device 100 to proceed to activate the heart rate sensor at block 720 and sense the user's heart rate at block 730. Fitness tracking device 100 may opportunistically collect these heart rate measurements to be used for determining parameters used for estimating energy expenditure.

In some embodiments, calibration method 700 may begin at block 710E. The fitness tracking device 100 may display—or respond to an app's request to display—heart rate information, such as the user's current heart rate. This signal may cause the fitness tracking device 100 to proceed to activate the heart rate sensor at block 720 and sense the user's heart rate at block 730. Fitness tracking device 100 may opportunistically collect these heart rate measurements to be used for determining parameters used for estimating energy expenditure.

In some embodiments, calibration method 700 may start at block 710F. The fitness tracking device 10—or an app running on the device—may analyze motion data from the motion sensing module 220 (FIG. 2) in the fitness tracking device 100. The fitness tracking device 100 or the app may determine that heart rate data may be required or may be helpful in light of the analyzed motion data. For example, the fitness tracking device 100 may be able to determine from analyzing motion data the user has been sitting down or has otherwise been at rest for a period of time (e.g., 30 minutes, 1 hour, 2 hours, etc.). The fitness tracking device 100 may determine that the user's heart rate may be at or close to the user's minimum (resting) heart rate (e.g., $HR_{min}$). Fitness tracking device 100 may proceed to activate the heart rate sensor at block 720 and sense the user's heart rate at 730 to collect heart rate measurements 740 that may provide a more accurate value for RHR or $HR_{min}$.

For another example, the fitness tracking device 100 may be able to determine from analyzing motion data that the user's wrist is relatively still, which may allow the heart rate sensing module 210 to obtain a more accurate heart rate measurement. Fitness tracking device 100 may opportunistically collect these heart rate measurements to be used for determining parameters used for estimating energy expenditure.

Other events not shown in FIG. 7 may trigger the beginning of calibration method 700 in addition to the events depicted at blocks 710A-710F. In some embodiments, the fitness tracking device 100 may receive contextual information from other devices indicating that a user is likely seated or otherwise at rest. For example, the contextual information might indicate that the user has been watching a long movie on a computer, television, or other device. Fitness tracking device 100 may proceed to activate the heart rate sensor at block 720 and sense the user's heart rate at 730 to collect heart rate measurements 740 that may provide a more accurate value for RHR or $HR_{min}$.

In some embodiments, the fitness tracking device 100 may analyze location information to determine that a user is likely seated or otherwise at rest. For example, the location information might indicate that the user has been located at a movie theater. Fitness tracking device 100 may proceed to activate the heart rate sensor at block 720 and sense the user's heart rate at 730 to collect heart rate measurements 740 that may provide a more accurate value for RHR or $HR_{min}$.

In some embodiments, the fitness tracking device 100 may analyze content information to determine whether a user is likely to have a relatively higher heart rate due to the content. For example, if the user is watching an action sequence in an action movie, the user may be physiologically aroused and have a relatively higher rate than the user's normal resting heart rate. Fitness tracking device 100 may opportunistically collect these heart rate measurements to be used for determining parameters used for estimating energy expenditure.

In some embodiments, the fitness tracking device 100 may analyze historical information (e.g., from the user's calendar) to determine that the user is likely to start an exercise session at a particular time or place. In anticipation of likely starting an exercise session, fitness tracking device 100 may proceed to activate the heart rate sensor at block 720 and sense the user's heart rate at 730 to collect heart rate measurements 740 that may provide a more accurate value for RHR or $HR_{min}$.

The aforementioned techniques for calibrating and tracking biometric parameters used to estimate energy expenditure are examples and other embodiments may include other techniques that may be used instead of or in addition to the aforementioned techniques. In some embodiments, the fitness tracking device 100 may store historical estimates of these parameters and interpolate or extrapolate new estimates based on the historical estimates in conjunction with heart rate measurements. For example, the fitness tracking device 100 may compute a weighted sum of one or more previous estimates with a value based on more recent measurements to determine the next estimated parameter value.

In some embodiments, parameter values may be inferred by extrapolating from the trajectory of heart rate measurements at the beginning of an exercise session (e.g., during a "ramp-up" or "onset" period), or by extrapolating from the trajectory of heart rate measurements after the exercise session has ended (e.g., during a "cool-down" period).

Additionally, as described above, some embodiments may use values for $HR_{max}$ and $\dot{V}O_2$max that have been calibrated or otherwise determined in Eq. 4 to determine a value for RHR. Analogously, if values for RHR and $HR_{max}$ have been calibrated or otherwise determined, some embodiments may use them in Eq. 4 to determine a value of $\dot{V}O_2$max. And, if values for RHR and $\dot{V}O_2$max have been calibrated or otherwise determined, some embodiments may use them in Eq. 4 to determine a value of $HR_{max}$.

Figure 8:
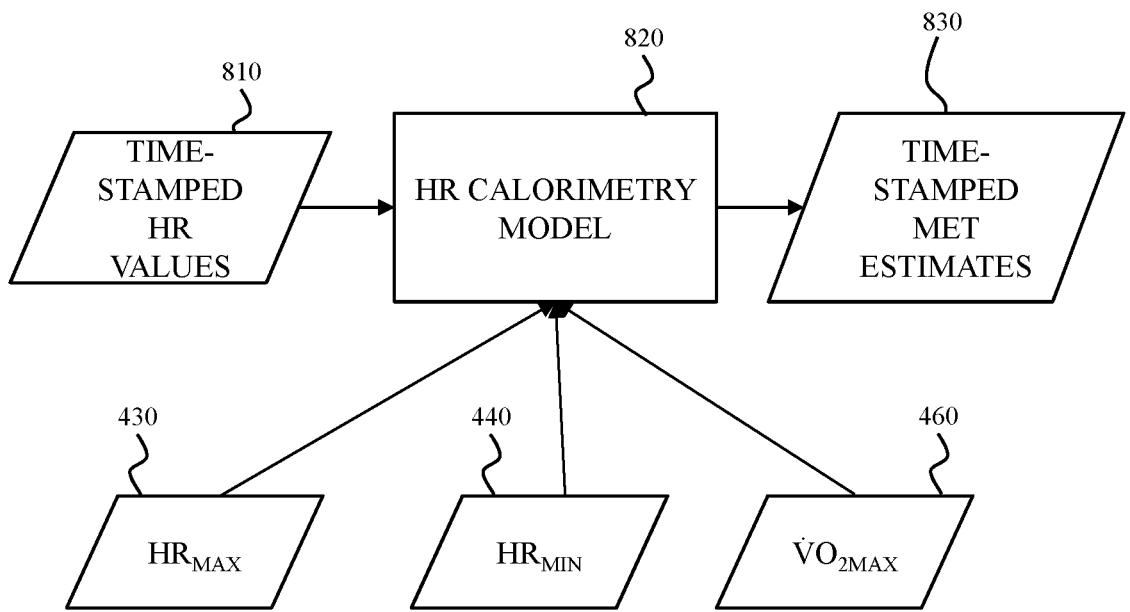
FIG. 8 is a flowchart showing estimation of METS using heart rate based calorimetry, according to some embodiments of the present disclosure.

FIG. 8 is a flowchart showing estimation of METS using heart rate based calorimetry, according to some embodiments of the present disclosure. FIG. 8 shows time-stamped HR values 810, HR calorimetry model 820, time-stamped MET estimates 830, $HR_{MAX}$ 440, $HR_{MIN}$ 450, and $\dot{V}O_2$max 460.

As described above, METs generally refers to how many calories a "typical" individual burns per unit of body mass per unit of time. When given serial heart rate measurements (e.g., time stamped HR values 410), estimation of METS 830 requires a user's $HR_{MAX}$ 440, $HR_{MIN}$ 450, and $\dot{V}O_2$max 460. These variables can be related by the techniques described above, and in particular to the techniques relating to determining energy expenditure 450 as described, for example, in FIG. 4. Because the calorimetry model is stationary, i.e., it does not change during the activity, each time-stamped HR value is applied to the model to obtain a corresponding time-stamped MET value.

Work Rate Based Determination of Energy Expenditure

In addition to using HR and $\dot{V}O_2$max to determine energy expenditure, as described above, energy expenditure can also be determined using work rate values. As described in more detail below, time stamped MET estimates can be determined by relating load, efficiency and measured work rate values.

Figure 9:
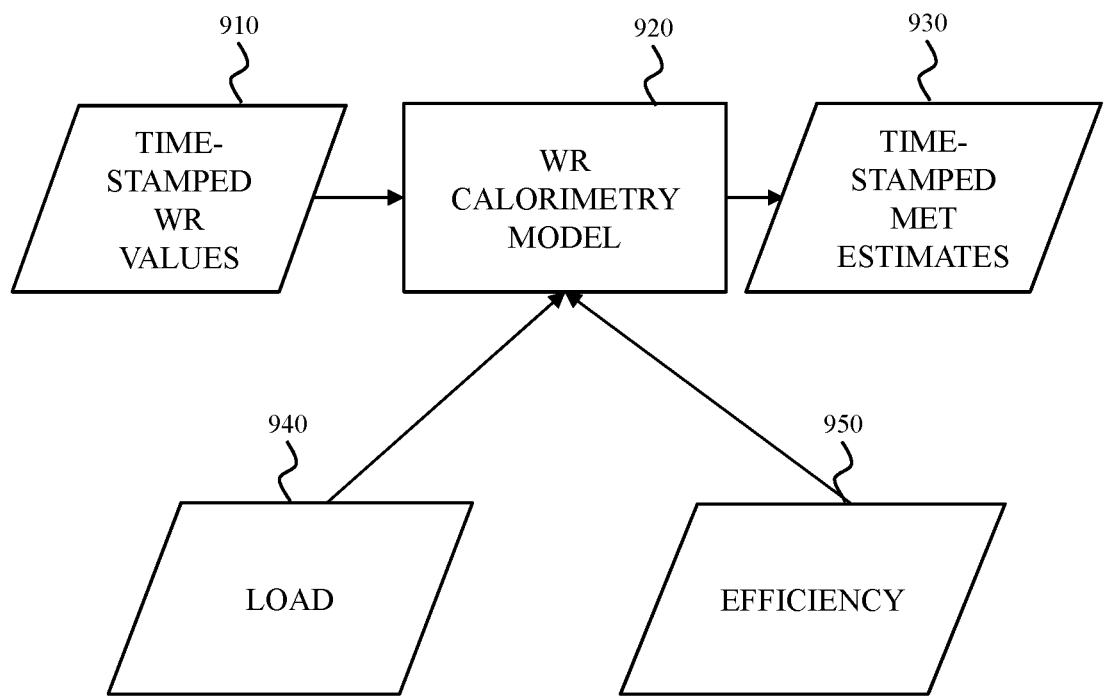
FIG. 9 is a flowchart showing estimation of METS using work rate based calorimetry, according to some embodiments of the present disclosure.

FIG. 9 is a flowchart showing estimation of METS using work rate based calorimetry, according to some embodiments of the present disclosure. FIG. 9 shows time-stamped WR values 910, WR calorimetry model 920, time-stamped MET estimates 930, load 940, and efficiency 950.

Time stamped MET estimates 930 can also be calculated by using time-stamped WR values 910, WR calorimetry model 920, load 940, and efficiency 950. Time-stamped WR values refer to serial measurements of speed, power, or effort exerted as part of an aerobic activity, i.e., workrate refers to a measurement of the physical work done as a result of the exercise. Load 940 refers generally to a resistance associated with exercise (e.g., incline, gear setting on bicycle). Efficiency 950 (also referred to herein as load efficiency) refers to a ratio of work output to work input during exercise. For example, as a user's body becomes more accustomed to a physical activity, the user's body becomes more efficient at that exercise and burns less calories (with all other variables such as speed and incline remaining equal). In some embodiments, the WR calorimetry model 920 relates WR values 910, load 940, and efficiency 950 using the following equation $$EE=(A+B*\text{load}*WR)/(\text{efficiency})$$

The choice of which calorimetry model (heart rate or work rate) to use for a given user and a given time can be based on multiple factors, including the availability or quality of the required input sources (e.g. GPS measurements, or HR measurements), the knowledge of the user (e.g. whether VO2max has been calibrated, or whether RHR or $HR_{max}$ are known), or the type of aerobic activity (e.g. whether load may be dynamically adjusted, as with many indoor exercise machines).

Joint Calibration of Load and $\dot{V}O_2$max

As described above, both load and $\dot{V}O_2$max can be used to determine energy expenditure. However, often times, neither load nor $\dot{V}O_2$max are precisely known. As described below with respect to Eq. 5, in some embodiments, the calories burned as determined from the time-stamped MET estimates calculated using a WR calorimetry model are equal to the calories burned as determined by time-stamped MET estimates calculated using a HR calorimetry model, over a sufficient time interval to allow for physiological dynamics. As both load and $\dot{V}O_2$max can be used to determine energy expenditure, load and $\dot{V}O_2$max can be related using the following equation, $$\text{Load}*\int_t WR_{mets}=VO_{2max}*\int_t HR_{mets} \qquad (\text{Eq. 5})$$

where WRmets refers to work rate METS and HRmets refers to heart rate METS.

As described above, one problem in the prior art is that calibration of load requires a known $\dot{V}O_2$max, while calibration of $\dot{V}O2$max requires a known load. To solve this problem, the present disclosure provides systems and methods of jointly calibrating load and $\dot{V}O_2$max, as described in more detail in the figures that follow.

Figure 10:
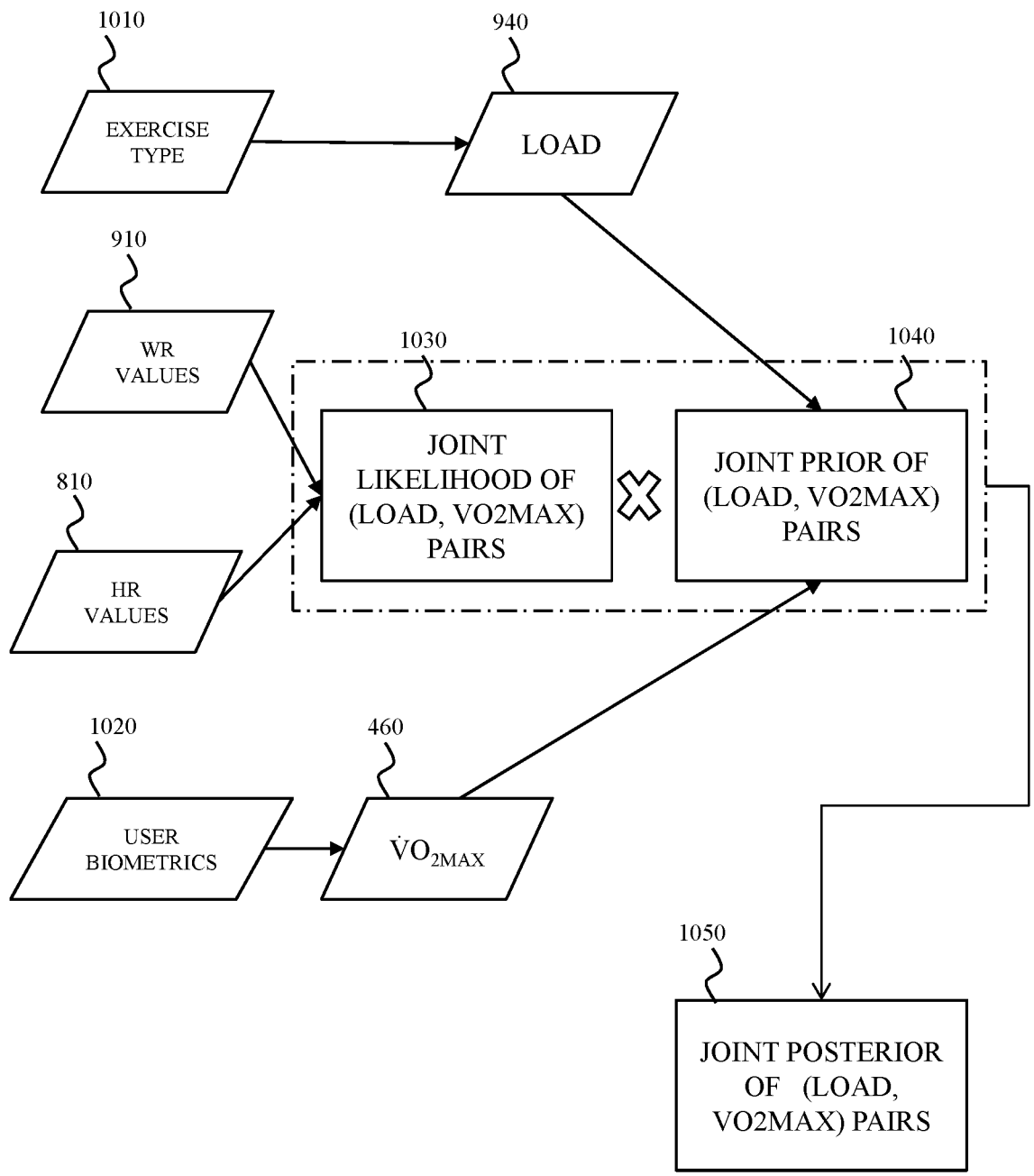
FIG. 10 is a flowchart showing a joint estimation of load and $\dot{V}O_2max$, according to some embodiments of the present disclosure.

FIG. 10 is a flowchart showing a joint estimation of load and $\dot{V}O_2$max, according to some embodiments of the present disclosure. FIG. 10 shows exercise type 1010, time-stamped WR values 910, time-stamped HR values 810, user biometrics 1020, load 940, $\dot{V}O_2$max 460, computing joint likelihood of (load, $\dot{V}O_2$max) pairs 1030, computing joint prior of (load, $\dot{V}O_2$max) pairs 1040, and computing joint posterior of (load, $\dot{V}O_2$max) pairs 1050.

Priors refers to known information, for example, the system has priors over load (based on the type of activity— e.g., running, cycling) and VO2max (based on user biometrics or activity levels) individually. In order to perform joint calibration, the prior over both values of load and $\dot{V}O_2$max should be known simultaneously. The simplest model assumes independence, e.g., load and $\dot{V}O_2$max vary independently of each other, in which case Prior(load, vo2max) =Prior(load)*Prior(vo2max). However, this may not be the case in all scenarios (for example, fitter users may be more likely to use higher loads on an elliptical, or they may be more likely to have expensive, low-resistance bicycles for outdoor cycling). Joint-likelihood is a statistical model that relates the probability of observing certain (WR, HR) pairs given the (load, $\dot{V}O_2$max) values. Joint posterior refers to the residual uncertainty of (load, $\dot{V}O_2$max) after observing all the data.

As described above, exercise type 1010 can refer to any form of aerobic activity, including but not limited to running, walking, biking, swimming, dancing, etc. User biometrics 1020 can include a user's age, gender, height, and weight. Exercise type 1010 can help to inform prior over load 940. User biometrics 1020 can help to inform prior over $\dot{V}O_2$max 460, through use of the Jackson equation (Jackson, A. S., Blair, S. N., Mahar, M. T., Wier, L. T., Rossand, R. M., & Stuteville, J. E. (1990), "Prediction of functional aerobic capacity without exercise testing", Medicine and Science in Sports and Exercise, 22(6), 863-870), which measures $\dot{V}O_2$max using a regression equation which takes into account age, gender, BMI, and activity levels, with a fair amount of residual uncertainty (15-20%).

Each of load 940 and $\dot{V}O_2$max 460 may be expressed as a probability distribution, as explained in more detail in the description accompanying FIG. 11 below. For example, the load in running is directly a result of internal resistive forces to running plus any additional weight the user may be carrying. The load in outdoor cycling is related to the rolling resistance, the weight of the bicycle, and the wind resistance. The load in elliptical workouts is the unknown machine resistance. The uncertainty/range of load in each of these activities can be estimated by looking at large population of user's exercise data.

Load 940 and $\dot{V}O_2$max 460 can also be used to compute a joint prior of the (load, $\dot{V}O_2$max) pairs 1040. As discussed above, a prior can refer to definite or known information about a variable. Since exercise type 1010 and user biometrics 1020 are known, received quantities from the user, each of load 940 and $\dot{V}O_2$max 460 can be expressed as a prior and can be represented by a distribution with a normalized variance and a mean based off the known exercise type 1010 and user biometrics 1020, respectively, in some embodiments. In other embodiments, the distributions may be empirically based and hence not entireley determined by the mean and variance (e.g., the representations may further rely on empirical distributions derived from large bodies of data collected in experimental conditions). In such cases, the distribution may be non-Gaussian and may be directly specified as opposed to a parametric distribution. The distribution data can be combined to form a joint prior, or joint probability, of the (load, $\dot{V}O_2$max) 1040. That is, the joint prior of the (load, $\dot{V}O_2$max) 1040 computes the joint probability of load 940 and $\dot{V}O_2$max 460. In the simplest case, independence of load and $\dot{V}O_2$max can be assumed. However, this may not be true in all cases, in which case specialized information about how the two variables typically relate for users performing a given activity type would need to be combined.

Further, time-stamped WR values 910 and time-stamped HR values 810 can be used to compute a joint likelihood of (load, $\dot{V}O_2$max) 1030. In some embodiments, computing a joint likelihood for load 940 and $\dot{V}O_2$max 460 includes determining the joint likelihood of any two observations associated with each of load 940 and $\dot{V}O_2$max 460. The likelihood of each of load 940 and $\dot{V}O_2$max 460 can be determined by calculating a mean μ and variance $\sigma^2$ for each of load 940 and $\dot{V}O_2$max 460 based off the data points received (e.g., time-stamped WR values 910, time-stamped HR values 810). In some implementations, the likelihood may be constructed such that:

$$\text{Prior}(HR\text{-}METs, WR\text{-}METs || \text{load}, \dot{V}O_2\text{max}) = 1/\text{alpha}*$$
$$[\text{load}*f(WR\text{-}METs) - \dot{V}O_2\text{max}*f(HR\text{-}METs)]$$

Joint likelihood of (load, V̇O₂max) 1030 are combined with joint prior of the (load, V̇O₂max) 1040 to produce a joint posterior of (load, V̇O₂max) 1050. In some embodiments, a posterior probability of an event is a conditional probability that is weighted by observed data. A posterior probability can be calculated for each of load 940 and V̇O₂max 460. The posterior probabilities of each of load 940 and V̇O₂max 460 can be combined to form a joint posterior of (load, V̇O₂max) pairs 1050 probability.

Figure 11A:
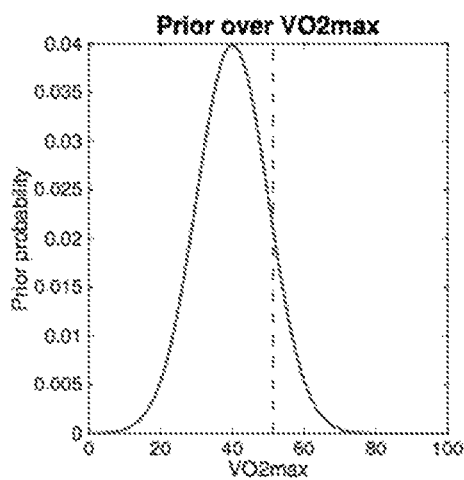
FIG. 11A is a graph of prior over $\dot{V}O_2max$, according to some embodiments of the present disclosure.
Figure 11D:
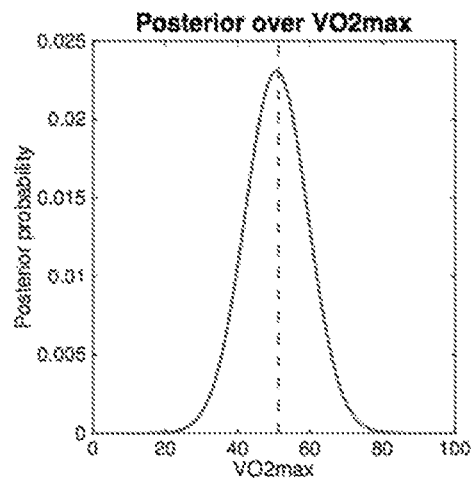
FIG. 11D is a graph of posterior over $\dot{V}O_2max$, according to some embodiments of the present disclosure.
Figure 11B:
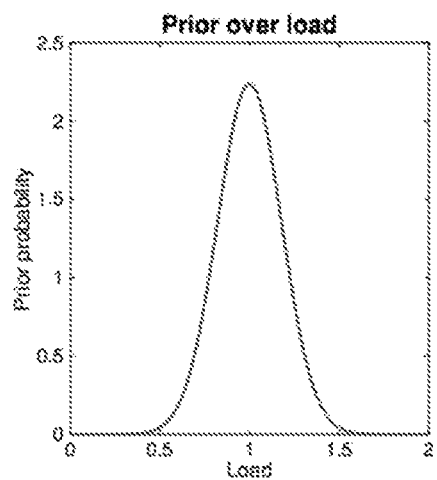
FIG. 11B is a graph of prior over of load, according to some embodiments of the present disclosure.
Figure 11E:
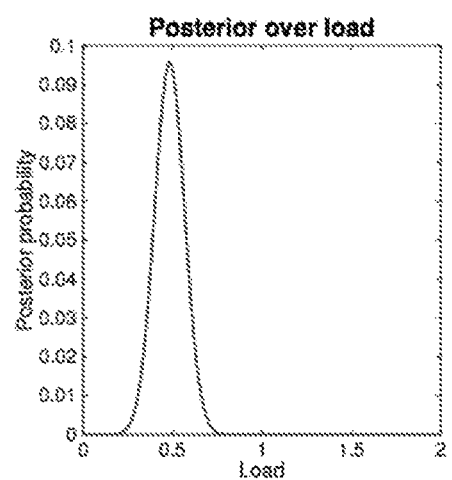
FIG. 11E is a graph of posterior over of load, according to some embodiments of the present disclosure.
Figure 11C:
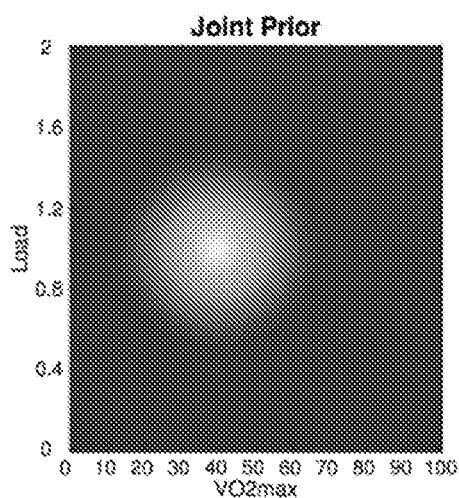
FIG. 11C is a graph of a joint prior, according to some embodiments of the present disclosure.
Figure 11F:
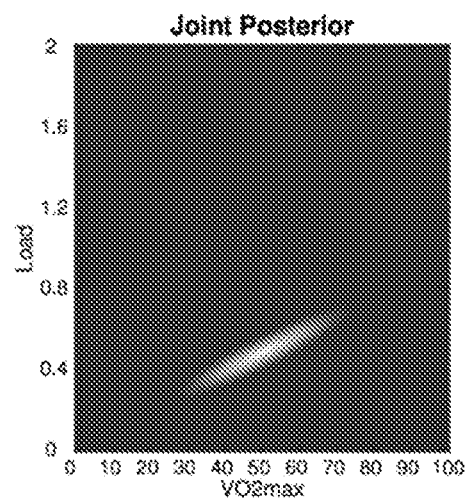
FIG. 11F is a graph of joint posterior, according to some embodiments of the present disclosure.

FIG. 11A is a graph of prior over V̇O₂max for a particular user, according to some embodiments of the present disclosure. FIG. 11B is a graph of prior over of load, for a particular user, according to some embodiments of the present disclosure. FIG. 11C is a graph of joint prior, for a particular user, according to some embodiments of the present disclosure. FIG. 11D is a graph of posterior over V̇O₂max, for a particular user, according to some embodiments of the present disclosure. FIG. 11E is a graph of posterior over of load, for a particular user, according to some embodiments of the present disclosure. FIG. 11F is a graph of joint posterior, for a particular user, according to some embodiments of the present disclosure.

FIGS. 11A-11F, taken together, comprise a graphical example for some of the systems and methods described herein. FIG. 11A shows a normalized distribution of prior over V̇O₂max. As described above, based on an user biometrics 1020, a normalized distribution can be created to express a prior over V̇O₂max 460 for a particular user. In this example, the mean $\mu$ is 40 ml/min/kg and the standard deviation $\sigma$ is 6. FIG. 11B shows a normalized distribution of prior over load. As described above, based on an exercise type 1010, a normalized distribution can be created to express a prior over load 940, for a particular user. In this example, the mean $\mu$ is 1 and the standard deviation $\sigma^2$ is 0.20.

FIG. 11C shows a joint prior probability of load 940 and V̇O₂max 460, assuming independence of load and VO2max. The joint probability shows a V̇O₂max of about 40 ml/min/kg and a load of about 1.

FIG. 11D-11F depict a revised measure of V̇O₂max and load for the same user, using the teaching of the present disclosure. FIG. 11D shows a distribution of posterior over V̇O₂max, and FIG. 11E shows a distribution of posterior over load. As described above, time-stamped WR values 910 and time-stamped HR values 810 are used to compute a joint likelihood of (load, V̇O₂max) pairs 1030. In some embodiments, computing a joint likelihood includes determining a mean $\mu$ and variance $\sigma^2$ for the difference between predicted WR-calories and HR-calories over a representative time scale (30 seconds, in this example). As described and shown below with respect to FIGS. 11D and 11E, the prior distributions of load 940 and V̇O₂max 460 can be weighted by the likelihood distributions of each of load 940 and V̇O₂max 460 to form the posterior over load and posterior over V̇O₂max distributions. In this example, the mean $\mu$ is 50 ml/min/kg (instead of 40, based only on the priors) and the standard deviation $\sigma$ is 2.2 in FIG. 11D. With reference to FIG. 11E, the mean $\mu$ is 0.5 (instead of 1, based only on the priors) and the standard deviation $\sigma$ is 0.08. By using the time stamped HR and WR values, a more accurate value for load and V̇O₂max can be estimated.

FIG. 11F shows a joint posterior probability of load 940 and V̇O₂max 460. Using a combination of both the joint likelihood of (load, V̇O₂max) pairs 1030 and the joint prior of the (load, V̇O₂max) pairs 1040 produces a more narrow and linear relationship relating load 940 and V̇O₂max 460. With this distribution, each of load and V̇O₂max can be estimated with greater accuracy by using this linear relationship.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes.

What is claimed is:

1. A method for jointly calibrating both a load of exercise and a user's aerobic capacity, the method comprising:
    retrieving, by a processor circuit of a device from a memory of the device, a prior probability distribution of the load of exercise;
    retrieving, by the processor circuit from the memory, a prior probability distribution of the user's aerobic capacity;
    determining, by the processor circuit, a joint prior probability of the load of exercise and the user's aerobic capacity based on the prior probability distribution of the load of exercise and the prior probability distribution of the user's aerobic capacity;
    measuring, by one or more motion sensors of the device, data indicative of a time-stamped work rate;
    measuring, by one or more heart rate sensors of the device, a time-stamped heart rate;
    determining, by the processor circuit, a joint likelihood of the load of exercise and the user's aerobic capacity based on the measured time-stamped work rate and the measured time-stamped heart rate;
    combining, by the processor circuit, the joint prior probability and the joint likelihood to produce a joint posterior probability;
    storing, by the processor circuit, the joint posterior probability in the memory of the device as a calibrated user calorie calculation parameter;
    after the storing, detecting, by at least one of the one or more motion sensors and the one or more heart rate sensors, new sensor data;
    detecting, by the processor circuit, an exercise activity from the new sensor data;
    performing, by the processor circuit, a calorie calculation by estimating a metabolic equivalent prediction based on the calibrated user calorie calculation parameter and the new sensor data; and
    outputting, by the processor circuit, the calorie calculation to a display of the device.

2. The method of claim 1, further comprising:
    receiving, by the processor circuit, a user input indicating an exercise type; and
    using, by the processor circuit, the exercise type to determine the prior probability distribution of the load of exercise.

3. The method of claim 2, where the processor circuit represents the prior probability distribution of the load of exercise by a distribution with a normalized variance and a mean based off the exercise type.

4. The method of claim 1, further comprising:
  determining, by the processor circuit, user biometrics; and
  using, by the processor circuit, the user biometrics to determine the prior probability distribution of the user's aerobic capacity.

5. The method of claim 4, where the processor circuit represents the prior probability distribution of the user's aerobic capacity by a distribution with a normalized variance and a mean based off the user biometrics.

6. The method of claim 1, further comprising:
  determining, by the processor circuit, a likelihood of an observation associated with the load of exercise and a likelihood of an observation associated with the user's aerobic capacity; and
  computing, by the processor circuit, the joint likelihood for the load of exercise and the user's aerobic capacity based on the likelihood of the observation associated with the load of exercise and the likelihood of the observation associated with the user's aerobic capacity.

7. The method of claim 6, where the processor circuit determines the likelihood of the observation associated with the load of exercise by calculating a mean and a variance based on the time-stamped work rate.

8. The method of claim 6, where the processor circuit determines the likelihood of the observation associated with the user's aerobic capacity by calculating a mean and a variance based on the time-stamped heart rate.

9. A system for jointly calibrating both a load of exercise and a user's aerobic capacity comprising:
  one or more motion sensors configured to execute instructions causing the one or more motion sensors to measure data indicative of a time-stamped work rate;
  one or more heart rate sensors configured to execute instructions causing the one or more heart rate sensors to measure a time-stamped heart rate;
  a display;
  a memory; and
  a processor circuit coupled to the one or more motion sensors, the one or more heart rate sensors, and the memory, the processor circuit configured to execute instructions causing the processor circuit to:
    retrieve, from the memory, a prior probability distribution of the load of exercise;
    retrieve, from the memory, a prior probability distribution of the user's aerobic capacity;
    determine a joint prior probability of the load of exercise and the user's aerobic capacity based on the prior probability distribution of the load of exercise and the prior probability distribution of the user's aerobic capacity;
    determine a joint likelihood of the load of exercise and the user's aerobic capacity based on the measured time-stamped work rate and the measured time-stamped heart rate;
    combine the joint prior probability and the joint likelihood to produce a joint posterior probability;
    store the joint posterior probability in the memory as a calibrated user calorie calculation parameter;
    after the storing, detect, by at least one of the one or more motion sensors and the one or more heart rate sensors, new sensor data;
    detect an exercise activity from the new sensor data;
    perform a calorie calculation by estimating a metabolic equivalent prediction based on the calibrated user calorie calculation parameter and the new sensor data; and
    output the calorie calculation to the display.

10. The system of claim 9, wherein the instructions further cause the processor circuit to:
  receive a user input indicating an exercise type; and
  use the exercise type to determine the prior probability distribution of the load of exercise.

11. The system of claim 10, wherein the instructions further cause the processor circuit to represent the prior probability distribution of the load of exercise by a distribution with a normalized variance and a mean based off the exercise type.

12. The system of claim 9, wherein the instructions further cause the processor circuit to:
  determine user biometrics; and
  use the user biometrics to determine the prior probability distribution of the user's aerobic capacity.

13. The system of claim 12, wherein the instructions further cause the processor circuit to represent the prior probability distribution of the user's aerobic capacity by a distribution with a normalized variance and a mean based off the user biometrics.

14. The system of claim 9, wherein the instructions further cause the processor circuit to:
  determine a likelihood of an observation associated with the load of exercise and a likelihood of an observation associated with the user's aerobic capacity; and
  determine the joint likelihood for the load of exercise and the user's aerobic capacity based on the likelihood of the observation associated with the load of exercise and the likelihood of the observation associated with the user's aerobic capacity.

15. The system of claim 14, wherein the instructions further cause the processor circuit to determine the likelihood of the observation associated with the load of exercise by calculating a mean and a variance based on the time-stamped work rate.

16. The system of claim 14, wherein the instructions further cause the processor circuit to determine the likelihood of the observation associated with the user's aerobic capacity by calculating a mean and a variance based on the time-stamped heart rate.

17. A mobile device comprising:
  one or more motion sensors configured to execute instructions causing the one or more motion sensors to measure data indicative of a time-stamped work rate;
  one or more heart rate sensors configured to execute instructions causing the one or more heart rate sensors to measure a time-stamped heart rate;
  a display;
  a memory; and
  a processor circuit coupled to the one or more motion sensors, the one or more heart rate sensors, and the memory, the processor circuit configured to execute instructions causing the processor circuit to:
    retrieve, from the memory, a prior probability distribution of the load of exercise;
    retrieve, from the memory, a prior probability distribution of the user's aerobic capacity;
    determine a joint prior probability of the load of exercise and the user's aerobic capacity based on the prior probability distribution of the load of exercise and the prior probability distribution of the user's aerobic capacity;
    determine a joint likelihood of the load of exercise and the user's aerobic capacity based on the measured time-stamped work rate and the measured time-stamped heart rate;

combine the joint prior probability and the joint likelihood to produce a joint posterior probability;

store the joint posterior probability in the memory as a calibrated user calorie calculation parameter;

after the storing, detect, by at least one of the one or more motion sensors and the one or more heart rate sensors, new sensor data;

detect an exercise activity from the new sensor data;

perform a calorie calculation by estimating a metabolic equivalent prediction based on the calibrated user calorie calculation parameter and the new sensor data; and output the calorie calculation to the display.

18. The mobile device of claim 17, wherein the instructions further cause the processor circuit to:

receive a user input indicating an exercise type; and use the exercise type to determine the prior probability distribution of the load of exercise.

19. The mobile device of claim 18, wherein the instructions further cause the processor circuit to represent the prior probability distribution of the load of exercise by a distribution with a normalized variance and a mean based off the exercise type.

20. The mobile device of claim 17, wherein the instructions further cause the processor circuit to:

determine user biometrics; and use the user biometrics to determine the prior probability distribution of the user's aerobic capacity.

21. The mobile device of claim 20, wherein the instructions further cause the processor circuit to represent the prior probability distribution of the user's aerobic capacity by a distribution with a normalized variance and a mean based off the user biometrics.

22. The mobile device of claim 17, wherein the instructions further cause the processor circuit to:

determine a likelihood of an observation associated with the load of exercise and a likelihood of an observation associated with the user's aerobic capacity; and determine the joint likelihood for the load of exercise and the user's aerobic capacity based on the likelihood of the observation associated with the load of exercise and the likelihood of the observation associated with the user's aerobic capacity.

23. The mobile device of claim 22, wherein the instructions further cause the processor circuit to determine the likelihood of the observation associated with the load of exercise by calculating a mean and a variance based on the time-stamped work rate.

24. The mobile device of claim 22, wherein the instructions further cause the processor circuit to determine the likelihood of the observation associated with the user's aerobic capacity by calculating a mean and a variance based on the time-stamped heart rate.

* * * * *